(12) United States Patent
Li et al.

(10) Patent No.: US 6,730,699 B2
(45) Date of Patent: May 4, 2004

(54) WATER SOLUBLE PACLITAXEL DERIVATIVES

(75) Inventors: Chun Li, Missouri City, TX (US); Sidney Wallace, Houston, TX (US); Dong-Fang Yu, Houston, TX (US); David Yang, Sugar Land, TX (US)

(73) Assignee: PG-TXL Company, L.P., Houston, TX (US)

( * ) Notice: Subject to any disclaimer, the term of this patent is extended or adjusted under 35 U.S.C. 154(b) by 31 days.

(21) Appl. No.: 10/300,031

(22) Filed: Nov. 20, 2002

(65) Prior Publication Data

US 2003/0166507 A1 Sep. 4, 2003

Related U.S. Application Data

(63) Continuation of application No. 10/153,818, filed on May 24, 2002, now Pat. No. 6,515,017, which is a continuation of application No. 09/530,601, filed on Jan. 11, 2001, now abandoned.

(51) Int. Cl.$^7$ ............................................. A61K 31/335
(52) U.S. Cl. ........................ 514/449; 514/510; 514/511; 424/486
(58) Field of Search ................................. 514/449, 510, 514/511; 424/1, 65, 9, 36, 486

(56) References Cited

U.S. PATENT DOCUMENTS

| | | | | | |
|---|---|---|---|---|---|
| 5,473,055 | A | * | 12/1995 | Mongeli et al. ............. | 530/329 |
| 5,626,862 | A | * | 5/1997 | Brem et al. ................. | 424/426 |
| 5,730,968 | A | * | 3/1998 | Butterfield et al. ....... | 424/78.37 |
| 5,776,925 | A | * | 7/1998 | Young et al. ................ | 514/185 |
| 5,846,565 | A | * | 12/1998 | Brem et al. ................. | 424/486 |
| 6,127,355 | A | * | 10/2000 | Greenwald et al. ......... | 514/183 |
| 6,218,367 | B1 | * | 4/2001 | Jacob .......................... | 514/25 |
| 6,262,107 | B1 | * | 7/2001 | Li et al. ..................... | 514/449 |

OTHER PUBLICATIONS

Li et al., "Enhancement of Tumor Radioresponse of A Murine Ovarian Carcinoma By Poly(L–Glutamic Acid)–Paclitaxel Conjugate", *CTI 9$^{th}$ Annual International Symposium on Recent Advances in Drug Delivery Systems*, Feb. 22–25, 1999, (2 pages).

Ke et al., "Schedule–Independent Radiosensitization of a Murine Ovarian Oca–1 Tumor by PG–TXL", *CTI Proceedings of the American Association for Cancer Research*, Vol 40, # 4223, Ref. 248, Mar. 1999 (1 page).

Li et al., "Water–Soluble Polyglutamic Acid–Paclitaxel Conjugate (PGA–Paclitaxel): Antiumour Regression in Rats Braeing 13762 Mammary Carcinoma", *Pharmaceutical Research*, Sep. 1996, vol. 13, No. 9, p. S–368, Abstract PDD 7541, see entire abstract.

* cited by examiner

*Primary Examiner*—James H Reamer
(74) *Attorney, Agent, or Firm*—Foley & Lardner

(57) ABSTRACT

Disclosed are water soluble compositions of paclitaxel and docetaxel formed by conjugating the paclitaxel or docetaxel to a water soluble polymer such as poly-glutamic acid, poly-aspartic acid or poly-lysine. Also disclosed are methods of using the compositions for treatment of tumors, auto-immune disorders such as rheumatoid arthritis. Other embodiments include the coating of implantable stents for prevention of restenosis.

25 Claims, 17 Drawing Sheets

Paclitaxel: R1=R2=H

PEG-Paclitaxel:
    R1=-COCH$_2$CH$_2$CONHCH$_2$CH$_2$(OCH$_2$CH$_2$)$_n$OCH$_3$
    R2=H 7-DTPA-paclitaxel:
    R1=H
    R2=

2'-DTPA-paclitaxel:
    R1=         R2=H

WATER SOLUBLE PACLITAXEL DERIVATIVES

CROSS-REFERENCE TO RELATED PATENT APPLICATIONS

This is a Continuation Application of application Ser. No. 10/153,818, filed May 24, 2002, which is in turn a continuation of application Ser. No. 09/530,601, filed Jan. 11, 2001 and is based on PCT/US99/06870, filed Mar. 30, 1999, which claims priority on U.S. application Ser. No. 09/050,662, filed Mar. 30, 1998.

FIELD OF THE INVENTION

The present invention relates generally to the fields of pharmaceutical compositions to be used in the treatment of cancer, autoimmune diseases and restenosis. The present invention also relates to the field of pharmaceutical preparations of anticancer agents such as paclitaxel (Taxol™) and docetaxel (Taxotere), in particular making paclitaxel water soluble by conjugating the drug to water soluble moieties.

BACKGROUND OF THE INVENTION

Paclitaxel, an anti-microtubule agent extracted from the needles and bark of the Pacific yew tree, *Taxus brevifolia*, has shown a remarkable anti-neoplastic effect in human cancer in Phase I studies and early Phase II and III trials (Horwitz et at, 1993). This has been reported primarily in advanced ovarian and breast cancer. Significant activity has been documented in small-cell and non-small cell lung cancer, head and neck cancers, and in metastatic melanoma. However, a major difficulty in the development of paclitaxel for clinical trial use has been its insolubility in water.

Docetaxel is semisynthetically produced from 10-deacetyl baccatin III, a noncytotoxic precursor extracted from the needles of *Taxus baccata* and esterified with a chemically synthesized side chain (Cortes and Pazdur, 1995). Various cancer cell lines, including breast, lung, ovarian, and colorectal cancers and melanomas have been shown to be responsive to docetaxel. In clinical trials, docetaxel has been used to achieve complete or partial responses in breast, ovarian, head and neck cancers, and malignant melanoma.

Paclitaxel is typically formulated as a concentrated solution containing paclitaxel, 6 mg per milliliter of Cremophor EL (polyoxyethylated castor oil) and dehydrated alcohol (50% v/v) and must be further diluted before administration (Goldspiel, 1994). Paclitaxel (Taxol™) has shown significant activity in human cancers, including breast, ovarian, non-small cell lung, and head and neck cancers (Rowinsky and Donehower, 1995). It has also shown significant activity in patients with advanced breast cancer who had been treated with multiple chemotherapeutic agents (Foa et al., 1994). As with most chemotherapeutic agents, however, the maximum tolerated dose of paclitaxel is limited by toxicity. In humans, paclitaxel's major toxic effect at doses of 100–250 mg/m$^2$ is granulocytopenia (Holmes et al., 1995); symptomatic peripheral neuropathy is its principal nonhematologic toxicity (Rowinsky et al., 1993).

The amount of Cremophor EL necessary to deliver the required doses of paclitaxel is significantly higher than that administered with any other drug that is formulated in Cremophor. Several toxic effects have been attributed to Cremophor, including vasodilatation, dyspnea, and hypotension. This vehicle has also been shown to cause serious hypersensitivity in laboratory animals and humans (Weiss et al., 1990). In fact, the maximum dose of paclitaxel that can be administered to mice by i.v. bolus injection is dictated by the acute lethal toxicity of the Cremophor vehicle (Eiseman et al., 1994). In addition, Cremophor EL, a surfactant, is known to leach phthalate plasticizers such as di(2-ethylhexyl)phthalate (DEHP) from the polyvinylchloride bags and intravenous administration tubing. DEHP is known to cause hepatotoxicity in animals and is carcinogenic in rodents. This preparation of paclitaxel is also shown to form particulate matter over time and thus filtration is necessary during administration (Goldspiel, 1994). Therefore, special provisions are necessary for the preparation and administration of paclitaxel solutions to ensure safe drug delivery to patients, and these provisions inevitably lead to higher costs.

Prior attempts to obtain water soluble paclitaxel have included the preparation of prodrugs of paclitaxel by placing solubilizing moieties such as succinate, sulfonic acid, amino acids, and phosphate derivatives at the 2'-hydroxyl group or at the 7-hydroxyl position (Deutsch et al., 1989; Mathew et al., Zhao and Kingston, 1991, 1992; Nicolaou et al., 1993; Vyas et al., 1995, Rose et al., 1997). While some of these prodrugs possess adequate aqueous solubility, few have antitumor activity comparable to that of the parent drug (Deutsch et al., 1989; Mathew et al., 1992; Rose et al., 1997). Several of these derivatives are not suitable for i.v. injection because of their instability in aqueous solution at neutral pH. For example, Deutsch et al. (1989) report a 2'-succinate derivative of paclitaxel, but water solubility of the sodium salt is only about 0.1% and the triethanolamine and N-methylglucamine salts were soluble at only about 1%. In addition, amino acid esters were reported to be unstable. Similar results were reported by Mathew et al. (1992).

Recently, Nicolaou et al. (1993) reported the synthesis and in vitro biological evaluation of a novel type of prodrug termed "protaxols". These compounds possess greater aqueous solubility and are converted to paclitaxel as the active drug through an intramolecular hydrolysis mechanism. However, no in vivo data on the antitumor activity of protaxols are yet available. Greenwald et al. reported the synthesis of highly water-soluble 2' and 7-polyethylene glycol esters of paclitaxel (Greenwald et al., 1994). Using the strategy of polymer linkage, others have developed water-soluble polyethylene glycol (PEG)-conjugated paclitaxel (Li et al., 1996; Greenwald et al., 1996). Although these conjugates have excellent water solubility, their therapeutic efficacies are not better than free paclitaxel. Moreover, PEG has only two reactive functional groups at each end of its polymer chain, which effectively limit the amount of paclitaxel that PEG could carry (U.S. Pat. No. 5,362,831).

Other attempts to solve these problems have involved microencapsulation of paclitaxel in both liposomes and nanospheres (Bartoni and Boitard, 1990). The liposome formulation was reported to be as effective as free paclitaxel, however only liposome formulations containing less than 2% paclitaxel were physically stable (Sharma and Straubinger, 1994). Unfortunately, the nanosphere formulation proved to be toxic. There is still a need therefore for a water soluble paclitaxel formulation that can deliver effective amounts of paclitaxel and docetaxel without the disadvantages caused by the insolubility of the drug.

Another obstacle to the widespread use of paclitaxel is the limited resources from which paclitaxel is produced, causing paclitaxel therapy to be expensive. A course of treatment may cost several thousand dollars, for example. There is the added disadvantage that not all tumors respond to paclitaxel therapy, and this may be due to the paclitaxel not getting into the tumor. There is an immediate need, therefore, for effective formulations of paclitaxel and related drugs that are water soluble with long serum half lives for treatment of tumors, autoimmune diseases such as rheumatoid arthritis, as well as for the prevention of restenosis of vessels subject to traumas such as angioplasty and stenting.

SUMMARY OF THE INVENTION

The present invention seeks to overcome these and other drawbacks inherent in the prior art by providing compositions comprising a chemotherapeutic and/or antiangiogenic drug, such as paclitaxel, docetaxel, or other taxoid conjugated to a water soluble polymer such as a water soluble polyamino acid, or to a water soluble metal chelator. It is a further embodiment of the present invention that a composition comprising a conjugate of paclitaxel and poly-glutamic acid has surprising antitumor activity in animal models, and further that this composition is demonstrated herein to be a new species of taxane that has pharmaceutical properties different from that of paclitaxel. These compositions are shown herein to be surprisingly effective as anti-tumor agents against exemplary tumor models, and are expected to be at least as effective as paclitaxel, docetaxel, or other taxoid against any of the diseases or conditions for which taxanes or taxoids are known to be effective. The compositions of the invention provide water soluble taxoids to overcome the drawbacks associated with the insolubility of the drugs themselves, and also provide the advantages of improved efficacy and controlled release so that tumors are shown herein to be eradicated in animal models after a single intravenous administration, as well as providing a novel taxane. Poly-(l-glutamic acid) conjugated paclitaxel is shown in the examples hereinbelow to have a novel drug activity, in addition to having improved the delivery to the tumor and providing a controlled release.

The methods described herein could also be used to make water soluble polymer conjugates of other therapeutic agents, contrast agents and drugs, including paclitaxel, tamoxifen, Taxotere, etopside, teniposide, fludarabine, doxorubicin, daunomycin, emodin, 5-fluorouracil, FUDR, estradiol, camptothecin, retinoids, verapamil, epothilones cyclosporin, and other taxoids. In particular, those agents with a free hydroxyl group would be conjugated to the polymers by similar chemical reactions as described herein for paclitaxel. Such conjugation would be well within the skill of a routine practitioner of the chemical art, and as such would fall within the scope of the claimed invention. Those agents would include, but would not be limited to etopside, teniposide, camptothecin and the epothilones. As used herein, conjugated to a water soluble polymer means the covalent bonding of the drug to the polymer or chelator.

It is also understood that the water soluble conjugates of the present invention may be administered in conjunction with other drugs, including other anti-tumor or anticancer drugs. Such combinations are known in the art. The water soluble paclitaxel, docetaxel, or other taxoid, or in preferred embodiments the poly-(l-glutamic) acid conjugated paclitaxel (PG-TXL), of the present invention may, in certain types of treatment, be combined with a platinum drug, an antitumor agent such as doxorubicin or daunorubicin, for example, or other drugs that are used in combination with Taxol™ or combined with external or internal irradiation, that is to say, radiation administered by an external radiation source, or administered systemically, for example, by injection or ingestion of radioactive materials, such as a radioisotope containing formulation.

Conjugation of chemotherapeutic drugs to polymers is an attractive approach to reduce systemic toxicity and improve the therapeutic index. Polymers with molecular mass larger than 30 kDa do not readily diffuse through normal capillaries and glomerular endothelium, thus sparing normal tissue from irrelevant drug-mediated toxicity (Maeda and Matsumura, 1989; Reynolds, 1995). On the other hand, it is well established that malignant tumors often have disordered capillary endothelium and greater permeability than normal tissue vasculature (Maeda and Matsumura, 1989; Fidler et al., 1987). Tumors often lack a lymphatic vasculature to remove large molecules that leak into the tumor tissue (Maeda and Matsumura, 1989). Thus, a polymer-drug conjugate that would normally remain in the vasculature may selectively leak from blood vessels into tumors, resulting in tumor accumulation of active therapeutic drug. The water soluble polymers, such as, in preferred embodiments PG-TXL, may have pharmacological properties different from non-conjugated drugs (i.e. paclitaxel). Additionally, polymer-drug conjugates may act as drug depots for sustained release, producing prolonged drug exposure to tumor cells. Finally, water soluble polymers (e.g., water soluble polyamino acids) may be used to stabilize drugs, as well as to solubilize otherwise insoluble compounds. At present, a variety of synthetic and natural polymers have been examined for their ability to enhance tumor-specific drug delivery (Kopecek, 1990, Maeda and Matsumura, 1989). However, only a few are known by the present inventors to be currently undergoing clinical evaluation, including SMANCS in Japan and HPMA-Dox in the United Kingdom (Maeda, 1991; Kopecek and Kopeckova, 1993).

In the present disclosure, a taxoid is understood to mean those compounds that include paclitaxels and docetaxel, and other chemicals that have the taxane skeleton (Cortes and Pazdur, 1995), and may be isolated from natural sources such as the Yew tree, or from cell culture, or chemically synthesized molecules, and a preferred taxane is a chemical of the general chemical formula, $C_{47}H_{51}NO_{14}$, including [2aR-[2aα,4β,4αβ,6β,9α(αR,*,βS*), 11α, 12α, 12aα, 12βα,]]-β-(Benzoylamino)-α-hydroxybenzene propanoic acid 6, 12b,bis(acetyloxy)-12-(benzoyloxy)-2a,3,4,4a,5,6,9, 10,11,12,12a,12b-dodecahydro-4,11-dihydroxy-4a,8,13,13-tetramethyl-5-oxo-7,11-methano-1H-cyclodeca[3,4]benz-[1,2-b]oxet-9-yl ester. It is understood that paclitaxel and docetaxel are each more effective than the other against certain types of tumors, and that in the practice of the present invention, those tumors that are more susceptible to a particular taxoid would be treated with that water soluble taxoid or taxane conjugate.

In those embodiments in which the paclitaxel is conjugated to a water soluble metal chelator, the composition may further comprise a chelated metal ion. The chelated metal ion of the present invention may be an ionic form of any one of aluminum, boron, calcium, chromium, cobalt, copper, dysprosium, erbium, europium, gadolinium, gallium, germanium, holmium, indium, iridium, iron, magnesium, manganese, nickel, platinum, rhenium, rubidium, ruthenium, samarium, sodium, technetium, thallium, tin, yttrium or zinc. In certain preferred embodiments, the chelated metal ion will be a radionuclide, i.e. a radioactive isotope of one of the listed metals. Preferred radionuclides include, but are not limited to $^{67}Ga$, $^{68}Ga$, $^{111}In$, $^{99m}Tc$, $^{90}Y$, $^{114m}Sn$ and $^{193m}Pt$.

Preferred water soluble chelators to be used in the practice of the present invention include, but are not limited to, diethylenetriaminepentaacetic acid (DTPA), ethylenediaminetetraacetic acid (EDTA), 1,4,7,10-tetraazacyclododecane-N,N',N,"N"' tetraacetate (DOTA), tetraazacyclotetradecane-N,N',N' 'N"'-tetraacetic acid (TETA), hydroxyethylidene diphosphonate (HEDP), dimercaptosuccinic acid (DMSA), diethylenetriaminetetramethylenephosphonic acid (DTTP) and 1-(p-aminobenzyl)-DTPA, 1,6-diamino hexane-N,N,N',N'-tetraacetic acid, DPDP, and ethylenebis (oxyethylenenitrilo)-tetraacetic acid, with DTPA being the most preferred. A preferred embodiment of the present invention may also be a composition comprising $^{111}$In-DTPA paclitaxel, and Na-DTPA-paclitaxel.

In certain embodiments of the present invention, the paclitaxel, docetaxel, or other taxoid may be conjugated to a water soluble polymer, and preferably the polymer is conjugated to the 2' or the 7- hydroxyl or both of the paclitaxel, docetaxel, or other taxoid. Poly-glutamic acid (PG) is one polymer that offers several advantages in the present invention. First, it contains a large number of side chain carboxyl functional groups for drug attachment. Second, PG can be readily degraded by lysosomal enzymes to its nontoxic basic component, 1-glutamic acid, d-glutamic acid and di-glutamic acid. Finally, sodium glutamate has been reported to prevent manifestations of neuropathy induced by paclitaxel, thus enabling higher doses of paclitaxel to be tolerated (Boyle et al., 1996). Preferred polymers include, but are not limited to poly(l-glutamic acid), poly (d-glutamic acid), poly(dl-glutamic acid), poly(l-aspartic acid), poly(d-aspartic acid), poly(dl-aspartic acid), poly(l-lysine), poly(d-lysine), poly(dl-lysine), copolymers of the above listed polyamino acids with polyethylene glycol, polycaprolactone, polyglycolic acid and polylactic acid, as well as poly(2-hydroxyethyl 1-glutamine), chitosan, carboxymethyl dextran, hyaluronic acid, human serum albumin and alginic acid, with poly-glutamic acids being particularly preferred. At the lower end of molecular weight, the polymers of the present invention preferably have a molecular weight of about 1,000, about 2,000, about 3,000, about 4,000, about 5,000, about 6,000, about 7,000, about 8,000, about 9,000, about 10,000, about 11 ,000, about 12,000, about 13,000, about 14,000, about 15,000, about 16,000, about 17,000, about 18,000, about 19,000, about 20,000, about 21,000, about 22,000, about 23,000, about 24,000, about 25,000, about 26,000, about 27,000, about 28,000, about 29,000, about 30,000, about 31,000, about 32,000, about 33,000, about 34,000, about 35,000, about 36,000, about 37,000, about 38,000, about 39,000, about 40,000, about 41,000, about 42,000, about 43,000, about 44,000, about 45,000, about 46,000, about 47,000, about 48,000, about 49,000, to about 50,000 D. At the higher end of molecular weight, the polymers of the present invention preferably have a molecular weight of about 51,000, about 52,000, about 53,000, about 54,000, about 55,000, about 56,000, about 57,000, about 58,000, about 59,000, about 60,000, about 61,000, about 62,000, about 63,000, about 64,000, about 65,000, about 66,000, about 67,000, about 68,000, about 69,000, about 70,000, about 71,000, about 72,000, about 73,000, about 74,000, about 75,000, about 76,000, about 77,000, about 78,000, about 79,000, about 80,000, about 81,000, about 82,000, about 83,000, about 84,000, about 85,000, about 86,000, about 87,000, about 88,000, about 89,000, about 90,000, about 91,000, about 92,000, about 93,000, about 94,000, about 95,000, about 96,000, about 97,000, about 98,000, about 99,000, to about 100,000 D. Within these ranges, the ranges of molecular weights for the polymers are preferably of about 5,000 to about 100,000 D, with about 20,000 to about 80,000 being preferred, or even about 25,000 to about 50,000 being more preferred.

It is a further aspect of the invention that a composition of the invention such as PG-TXL may also be conjugated to a second lipophilic or poorly soluble antitumor agent such as camptothecin, epothilone, cisplatin, melphalan, Taxotere, etoposide, teniposide, fludarabine, verapamil, or cyclosporin, for example, or even to water soluble agents such as 5 fluorouracil (5 FU) or fluorodeoxyuridine (FUDR), doxorubicin or daunomycin.

It is understood that the compositions of the present invention may be dispersed in a pharmaceutically acceptable carrier solution as described below. Such a solution would be sterile or aseptic and may include water, buffers, isotonic agents or other ingredients known to those of skill in the art that would cause no allergic or other harmful reaction when administered to an animal or human subject. Therefore, the present invention may also be described as a pharmaceutical composition comprising a chemotherapeutic or anti-cancer drug such as paclitaxel, docetaxel, or other taxoid conjugated to a high molecular weight water soluble polymer or to a chelator. The pharmaceutical composition may include polyethylene glycol, poly-glutamic acids, poly-aspartic acids, poly-lysine, or a chelator, preferably DTPA. It is also understood that a radionuclide may be used as an anti-tumor agent, or drug, and that the present pharmaceutical composition may include a therapeutic amount of a chelated radioactive isotope.

In certain embodiments, the present invention may be described as a method of determining the uptake of a chemotherapeutic drug such as paclitaxel, docetaxel, or other taxoid by tumor tissue. This method may comprise obtaining a conjugate of the drug and a metal chelator with a chelated metal ion, contacting tumor tissue with the composition and detecting the presence of the chelated metal ion in the tumor tissue. The presence of the chelated metal ion in the tumor tissue is indicative of uptake by the tumor tissue. The chelated metal ion may be a radionuclide and the detection may be scintigraphic. The tumor tissue may also be contained in an animal or a human subject and the composition would then be administered to the subject.

The present invention may also be described in certain embodiments as a method of treating cancer in a subject. This method includes obtaining a composition comprising a chemotherapeutic drug such as paclitaxel, docetaxel, or other taxoid conjugated to a water soluble polymer or chelator and dispersed in a pharmaceutically acceptable solution and administering the solution to the subject in an amount effective to treat the tumor. Preferred compositions comprise paclitaxel, docetaxel, or other taxoid conjugated to a water soluble polyamino acids, including but not limited to poly (l-aspartic acid), poly (daspartic acid), or poly (dl-aspartic acid), poly (l-lysine acid), poly (d-lysine acid), or poly (di-lysine acid), and more preferably to poly (1-glutamic acid), poly (d-glutamic acid, or poly (dl-glutamic acid). The compositions of the invention are understood to be effective against any type of cancer for which the unconjugated taxoid is shown to be effective and would include, but not be limited to breast cancer, ovarian cancer, malignant melanoma, lung cancer, head and neck cancer. The compositions of the invention may also be used against gastric cancer, prostate cancer, colon cancer, leukemia, or Kaposi's Sarcoma. As used herein the term "treating" cancer is understood as meaning any medical management of a subject having a tumor. The term would encompass any inhibition of tumor growth or metastasis, or any attempt to inhibit, slow or abrogate tumor growth or metastasis. The method includes killing a cancer cell by non-apoptotic as well as apoptotic mechanisms of cell death. The method of treating a tumor may include some prediction of the paclitaxel or docetaxel uptake in the tumor prior to administering a therapeutic amount of the drug, by methods that include but are not limited to bolus injection or infusion, as well as intraarterial, intravenous, intraperitoneal, or intratumoral administration of the drug.

This method may include any of the imaging techniques discussed above in which a paclitaxel-chelator-chelated metal is administered to a subject and detected in a tumor. This step provides a cost effective way of determining that a particular tumor would not be expected to respond to DTPA-paclitaxel therapy in those cases where the drug does not get into the tumor. It is contemplated that if an imaging technique can be used to predict the response to paclitaxel and to identify patients that are not likely to respond, great expense and crucial time may be saved for the patient. The assumption is that if there is no reasonable amount of chemotherapeutic agent deposited in the tumor, the probability of tumor response to that agent is relatively small.

In certain embodiments the present invention may be described as a method of obtaining a body image of a subject. The body image is obtained by administering an effective amount of a radioactive metal ion chelated to a paclitaxel-chelator conjugate to a subject and measuring the scintigraphic signals of the radioactive metal to obtain an image.

The present invention may also be described in certain broad aspects as a method of decreasing at least one symptom of a systemic autoimmune disease comprising administering to a subject, having a systemic autoimmune disease an effective amount of a composition comprising paclitaxel or docetaxel conjugated to polymer, with polyamino acids being preferred and poly-glutamic acid being more preferred. Of particular interest in the context of the present disclosure is the treatment of rheumatoid arthritis, which is known to respond in some cases to paclitaxel when administered in the standard Cremophor formulation (U.S. Pat. No. 5,583,153, incorporated herein by reference). As in the treatment of tumors, it is contemplated that the effectiveness of the water soluble taxoids or taxane of the present invention will not be diminished by the conjugation to a water soluble moiety. Therefore, the compositions of the present invention are expected to be as effective as paclitaxel against rheumatoid arthritis. Paclitaxel is an antiangiogenic agent. Rheumatoid arthritis creates a collection of newly formed vessels which erode the adjacent joints. It is also understood that the taxoid or taxane compositions of the present invention may be used in combination with other drugs, such as an angiogenesis inhibitor (AGM-1470) (Oliver et al., 1994), or other anti-cancer drugs, such as methotrexate.

The finding that paclitaxel also inhibits restenosis after balloon angioplasty indicates that the water soluble paclitaxels and docetaxels of the present invention will find a variety of applications beyond direct parenteral administration (WO 9625176, incorporated herein by reference). For example, it is contemplated that water soluble paclitaxel will be useful as a coating for implanted medical devices, such as tubings, shunts, catheters, artificial implants, pins, electrical implants such as pacemakers, and especially for arterial or venous stents, including balloon-expandable sterits. In these embodiments it is contemplated that water soluble paclitaxel may be bound to an implantable medical device, or alternatively, the water soluble paclitaxel may be passively adsorbed to the surface of the implantable device. For example, stents may be coated with polymer-drug conjugates by dipping the stent in polymer-drug solution or spraying the stent with such a solution. Suitable materials for the implantable device should be biocompatible and non-toxic and may be chosen from the metals such as nickel-titanium alloys, steel, or biocompatible polymers, hydrogels, polyurethanes, polyethylenes, ethylenevinyl acetate copolymers, etc. In a preferred embodiment the water soluble paclitaxel, especially a PG-TXL conjugate, is coated onto a stent for insertion into an artery or vein following balloon angioplasty. The invention may be described therefore, in certain broad aspects as a method of inhibiting arterial restenosis or arterial occlusion following vascular trauma comprising administering to a subject in need thereof, a composition comprising paclitaxel or docetaxel conjugated to polyglutamic acid or other water soluble poly-amino acids. In the practice of the method, the subject may be a coronary bypass, vascular surgery, organ transplant or coronary or any other arterial angioplasty patient, for example, and the composition may be administered directly, intravenously, or even coated on a stent to be implanted at the sight of vascular trauma.

An embodiment of the invention is, therefore, an implantable medical device, wherein the device is coated with a composition comprising paclitaxel or docetaxel conjugated to poly-glutamic acids or water soluble polyamino acids in an amount effective to inhibit smooth muscle cell proliferation. A preferred device is a stent coated with the compositions of the present invention as described herein, and in certain preferred embodiments, the stent is adapted to be used during or after balloon angioplasty and the coating is effective to inhibit restenosis.

In certain preferred embodiments, the invention may be described as a composition comprising poly-glutamic acids conjugated to the 2' or 7 hydroxyl or both of paclitaxel, docetaxel, or other taxoids, or even a composition comprising water soluble polyamino acids conjugated to the 2' or 7 hydroxyl or both of paclitaxel, docetaxel or other taxoids.

As used herein, the terms "a poly-glutamic acid" or "poly-glutamic acids" include poly (1-glutamic acid), poly (d-glutamic acid) and poly (dl-glutamic acid), the terms "a poly-aspartic acid" or "poly-aspartic acids" include poly (l-aspartic acid), poly (d-aspartic acid), poly (dl-aspartic acid), the terms "a poly-lysine" or "poly-lysine" include poly (1-lysine), poly (d-lysine), poly (dl-lysine), and the terms "a water soluble polyamino acid," "water soluble polyamino acids," or "water soluble polymer of amino acids" include, but are not limited to, poly-glutamic acid, poly-aspartic acid, poly-lysine, and amino acid chains comprising mixtures of glutamic acid, aspartic acid, and/or lysine. In certain embodiments, the terms "a water soluble polyamino acid," "water soluble polyamino acids," or "water soluble polymer of amino acids" include amino acid chains comprising combinations of glutamic acid and/or aspartic acid and/or lysine, of either d and/or 1 isomer conformation. In certain preferred embodiments, such a "water soluble polyamino acid" contains one or more glutamic acid, aspartic acid, and/or lysine residues. Such "water soluble polyamino acids" may also comprise any natural, modified, or unusual amino acid described herein, as long as the majority of residues, i.e. greater than 50%, comprise glutamic acid and/or aspartic acid and/or lysine. In certain embodiments, a water soluble polymer of amino acids that contains more than one different type of amino acid residue is sometimes referred to herein as a "co-polymer".

In certain embodiments, various substitutions of naturally occurring, unusual, or chemically modified amino acids may be made in the amino acid composition of the "water soluble polyamino acids," and particularly in "poly-glutamic acids," to produce a taxoid-polyamino acid conjugate of the present invention and still obtain molecules having like or otherwise desirable characteristics of solubility and/or therapeutic efficacy. A polyamino acid such as poly-glutamic acid, poly-aspartic acid, poly-lysine, or water soluble amino acids chain or polymer comprising a mixture of glutamic acid, aspartic acid, and/or lysine, may, at the lower end of the amino acid substitution range, have about 1, about 2, about 3, about 4, about 5, about 6, about 7, about 8, about 9, about 10, about 12, about 13, about 14, about 15, about 16, about 17, about 18, about 19, about 20, about 21, about 22, about 23, about 24, or about 25 or more glutamic acid, aspartic acid, or lysine, residues, respectively, substituted by any of the naturally occurring, modified, or unusual amino acids described herein. In other aspects of the invention, a polyamino acid such as poly-glutamic acid, poly-aspartic acid, poly-lysine, or a poly-amino acid chain comprising a mixture of some or all of these three amino acids may, at the lower end, have about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, to about 25% or more glutamic acid, aspartic acid, or lysine residues, respectively, substituted by any of the naturally occurring, modified, or unusual amino acids described herein.

In further aspects of the invention, a polyamino acid such as poly-glutamic acid, poly-aspartic acid, or poly-lysine may, at the high end of the amino acid substitution range, have about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, to about 50% or so of the glutamic acid, aspartic acid, or lysine residues, respectively, substituted by any of the naturally occurring, modified, or unusual amino acids described herein, as long as the majority of residues comprise glutamic acid and/or aspartic acid and/or lysine. In amino acid substitution of the various water soluble amino acid polymers, residues with a hydrophilicity index of +1 or more are preferred.

In certain aspects of the invention, the amount of antitumor drug conjugated per water soluble polymer can vary. At the lower end, such a composition may comprise from about 1%, about 2%, about 3%, about 4%, about 5%, about 6%, about 7%, about 8°/a, about 9%, or about 10%, about 11%, about 12%, about 13%, about 14%, about 15%, about 16%, about 17%, about 18%, about 19%, about 20%, about 21% about 22%, about 23%, about 24%, to about 25% (w/w) antitumor drug relative to the mass of the conjugate. At the high end, such a composition may comprise from about 26%, about 27%, about 28%, about 29%, about 30%, about 31% about 32%, about 33%, about 34%, about 35%, about 36%, about 37%, about 38%, about 39%, to about 40% or more (w/w) antitumor drug relative to the mass of the conjugate. Preferred anti-tumor drugs include paclitaxel, docetaxel, or other taxoids, and preferred water soluble polymers include water soluble amino acid polymers.

In certain other aspects of the invention, the number of molecules of anti-tumor drug conjugated per molecule of water soluble polymer can vary. At the lower end, such a composition may comprise from about 1, about 2, about 3, about 4, about 5, about 6, about 7, about 8, about 9, about 10, about 11, about 12, about 13, about 14, about 15, about 16, about 17, about 18, about 19, to about 20 or more molecules of antitumor drug per molecule of water soluble polymer. At the higher end, such a composition may comprise from about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60 about 61, about 62, about 63, about 64, about 65, about 66, about 67, about 68, about 69, about 70, about 71, about 72, about 73, about 74, to about 75 or more molecules or more of antitumor drug per molecule of water soluble polymer. Preferred anti-tumor drugs include paclitaxel, docetaxel, or other taxoids, and preferred water soluble polymers include water soluble amino acid polymers. The preferred number of anti-tumor drug molecules conjugated per molecule of water soluble polymer is about 7 molecules of antitumor drug per molecule of water soluble polymer.

Water soluble amino acid polymers with various substitutions of residues conjugated to paclitaxel, docetaxel, or other taxoids are referred to as "biological functional equivalents". These "biologically functional equivalents" are part of the definition of "water soluble polyamino acids" that are conjugated to taxoids, and may be identified by the assays described herein as well as any applicable assay that is known to those of skill in the art to measure improved aqueous solubility relative to the unconjugated taxoid or taxoids used to produce the particular water soluble amino acid polymer-taxoid composition. In other aspects of the invention, "biological functional equivalents" of water soluble amino acid-taxoid polymers may be further identified by improved anti-tumor cell activity, relative to the anti-tumor cell activity of the unconjugated water soluble amino acid polymer used to produce the particular water soluble amino acid polymer-taxoid composition by the assays described herein as well as any applicable assay that is known to those of skill in the art. The term "biologically functional equivalents" as used herein to describe this aspect of the invention is further described in the detailed description of the invention.

Unless defined otherwise, all technical and scientific terms used herein have the same meaning as commonly understood by one of ordinary skill in the art to which this invention belongs. Also as used herein, the term "a" is understood to include the meaning "one or more". Although any methods and materials similar or equivalent to those described herein can be used in the practice or testing of the present invention, the preferred methods and materials are now described.

Figure 7A:
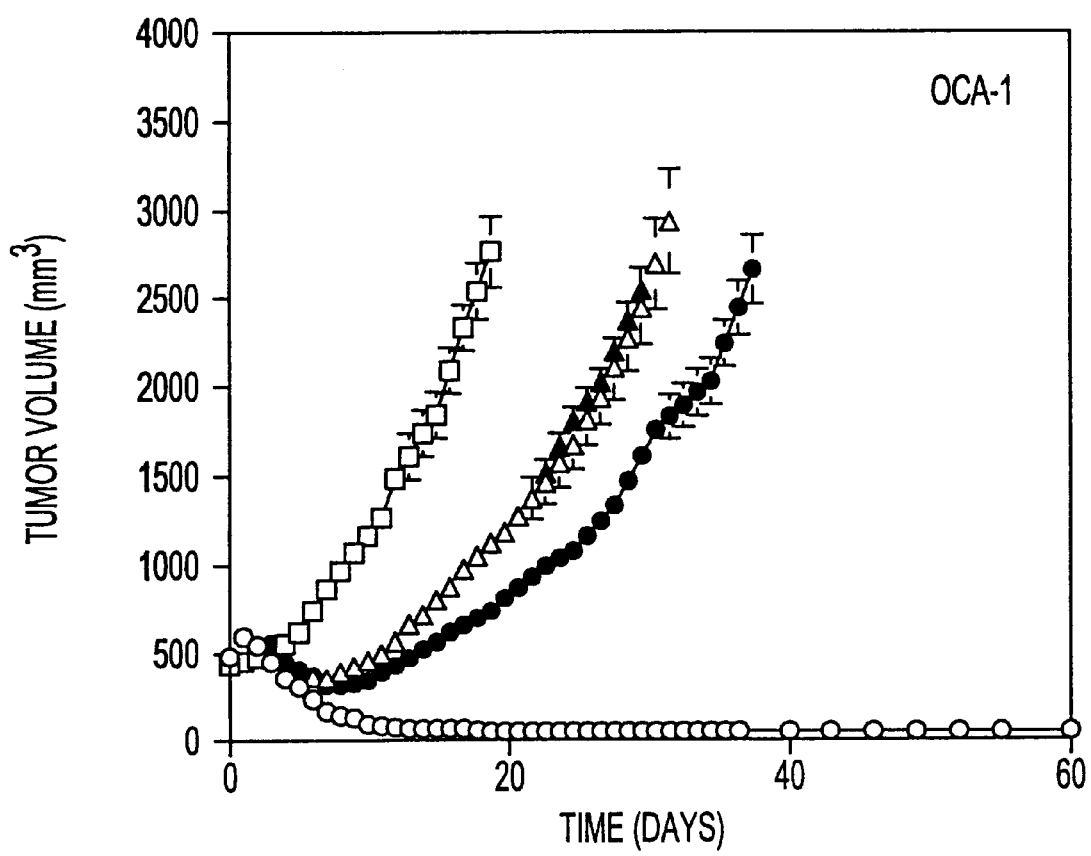

FIG. 7A. Anti-tumor effect of PG-TXL against syngeneic OCA-1 ovarian carcinoma tumor in female C3Hf/Kam mice. Drugs were injected intraveneously in a single dose. Data are presented as mean±standard deviation of tumor volumes. a, Mice bearing OCA-1 tumor were injected with -□-, PG control (800 mg/kg; n=9); -▲-, paclitaxel (80 mg/kg; n=7); -Δ-, paclitaxel (80 mg/kg) plus PG (800 mg/kg; n=5); -●-, PG-TXL (80 mg equiv. paclitaxel; n=6); or -○-, PG-TXL (160 mg equiv. paclitaxel/kg; n=26).

Figure 7B:
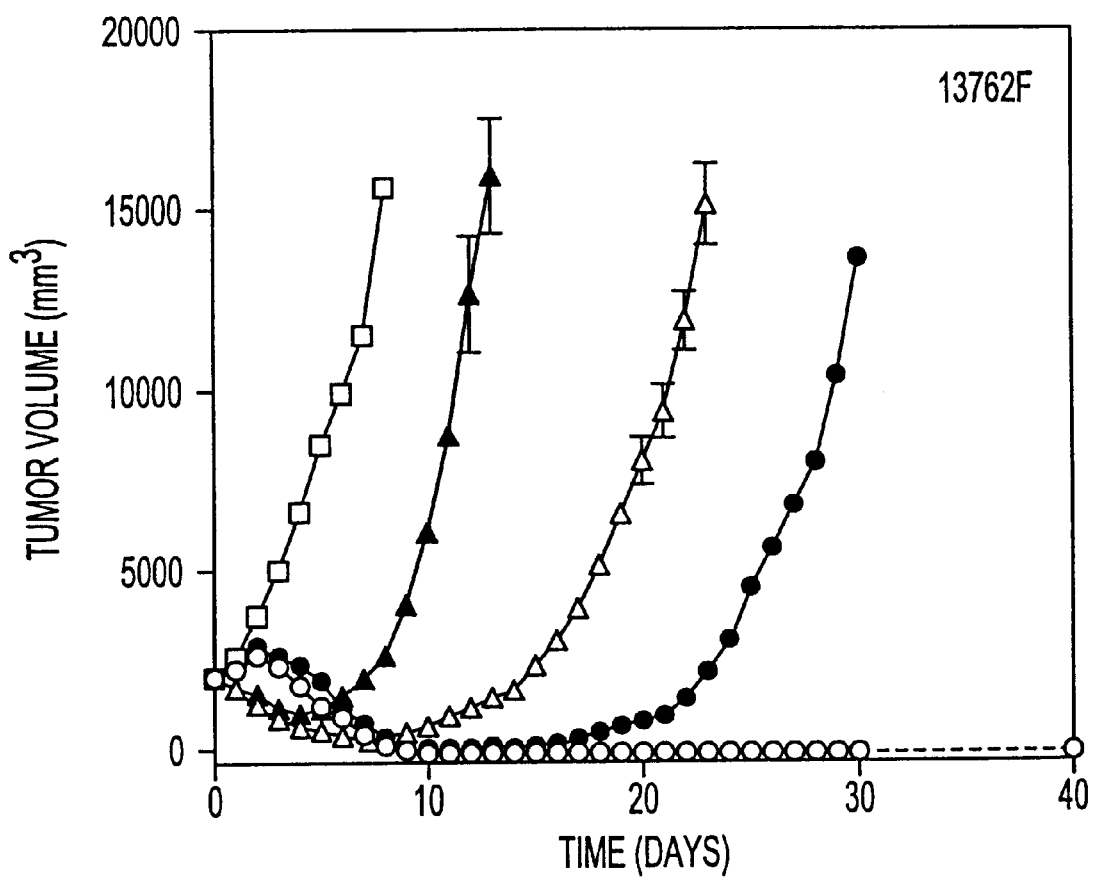

FIG. 7B. Anti-tumor effect of PG-TXL against 13762F tumor in female rats. -□- represents PG control (220 mg/kg; n=7), -▲- represents paclitaxel (20 mg/kg; n=5), -Δ- represents paclitaxel (40 mg/kg; n=7), -●- represents PG-TXL (20 mg equivalent paclitaxel/kg; n=5), -○- represents PG-TXL (40 mg or 60 mg equivalent paclitaxel/kg; n=9).

Figure 7C:
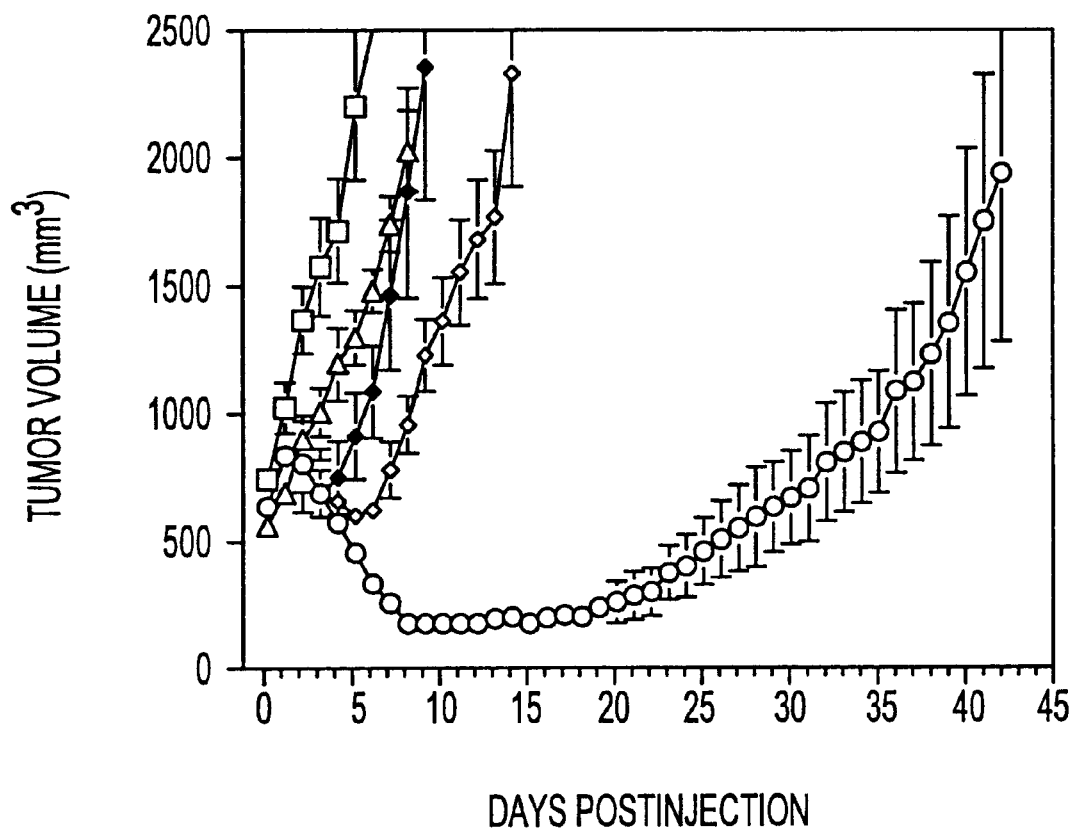

FIG. 7C. The antitumor effect of PG-TXL on mice bearing MCa-4 mammary carcinoma tumors. -□- represents the response to a single i.v. dose of saline, -Δ- represents the response to a single i.v. dose of PG (0.6 g/kg); -♦- represents response to PG-TXL (40 mg/kg),-◊- represents response to PG-TXL (60 mg equiv. paclitaxel/kg), -○- represents response to PG-TXL (120 mg/kg).

Figure 7D:
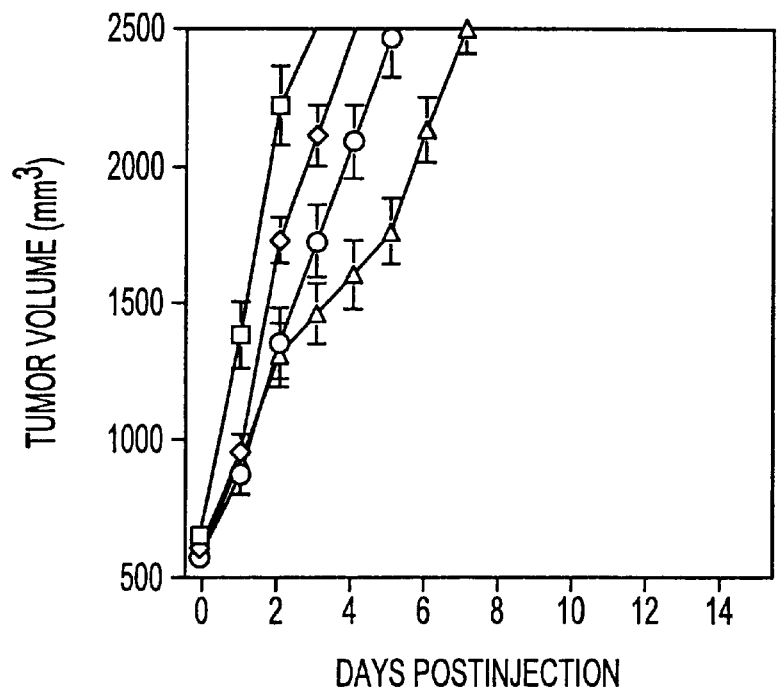

FIG. 7D. The antitumor effect of PG-TXL against soft-tissue sarcoma tumor (FSa-ll) in mice. -□- represents the response to a single i.v. dose of saline, -◊- represents the response to a single i.v. dose of PG (0.8 g/kg); -○- represents response to paclitaxel (80 mg/kg), -○- represents response to PG-TXL (160 mg equiv. Paclitaxel/kg).

Figure 7E:
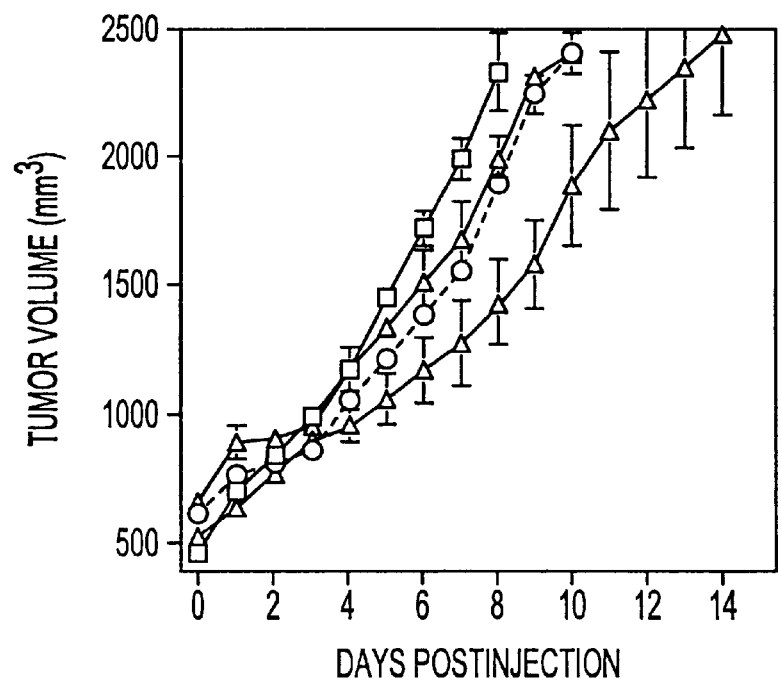

FIG. 7E. The antitumor effect of PG-TXL against syngeneic hepathcarcinoma tumor (HCa-I) in mice. -□- represents the response to a single i.v. dose of saline, -Δ- represents the response to a single i.v. dose of PG (0.8 g/kg); -○- represents response to PG-TXL (80 mg/kg), -Δ- represents response to PG-TXL (160 mg equiv. paclitaxel/kg).

Figure 8:
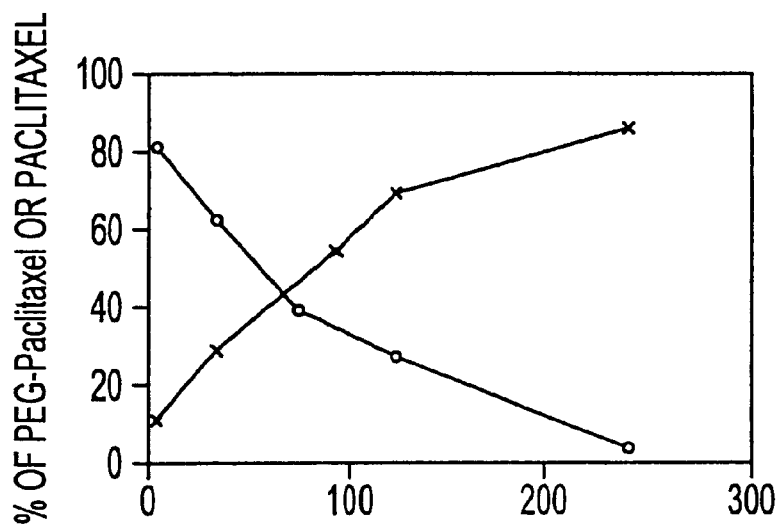

FIG. 8. Release profile of paclitaxel from PEG-paclitaxel in phosphate buffer (pH 7.4). Release profiles of paclitaxel (-X-); from PEG-paclitaxel (-○-) at pH 7.4 is shown.

Figure 9:
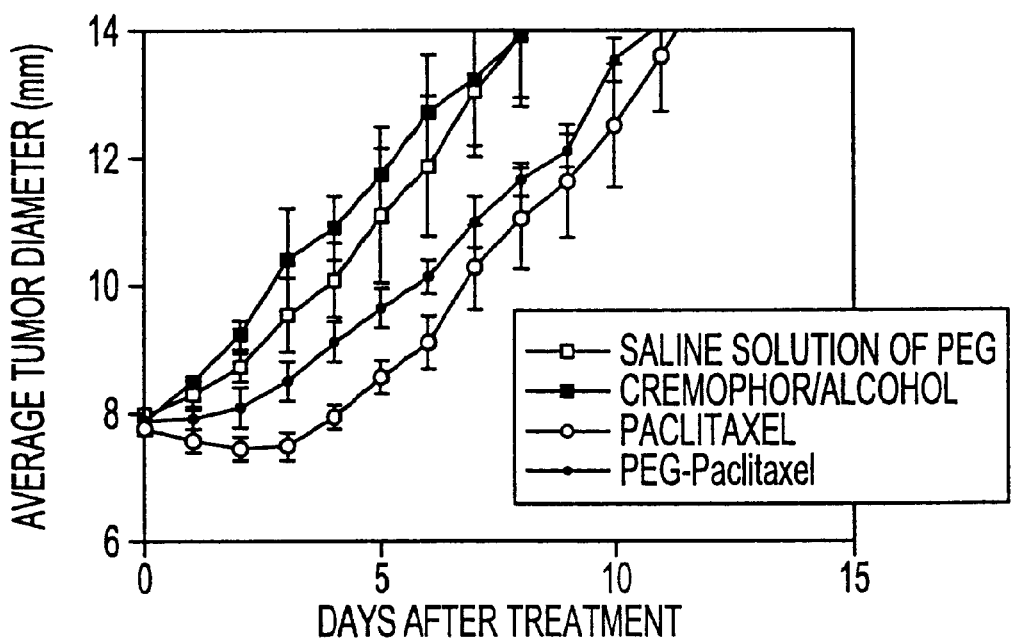

FIG. 9. Antitumor effect of PEG-paclitaxel on MCa-4 mammary tumors. -□- represents the response a single i.v. injection with a saline solution of PEG (60 mg/ml), -■- represents the response to the Cremophor/alcohol vehicle, -○- represents a single dose of 40 mg/kg body weight of paclitaxel, -●- represents PEG-paclitaxel at 40 mg equiv. paclitaxel/kg body weight.

Figure 10:
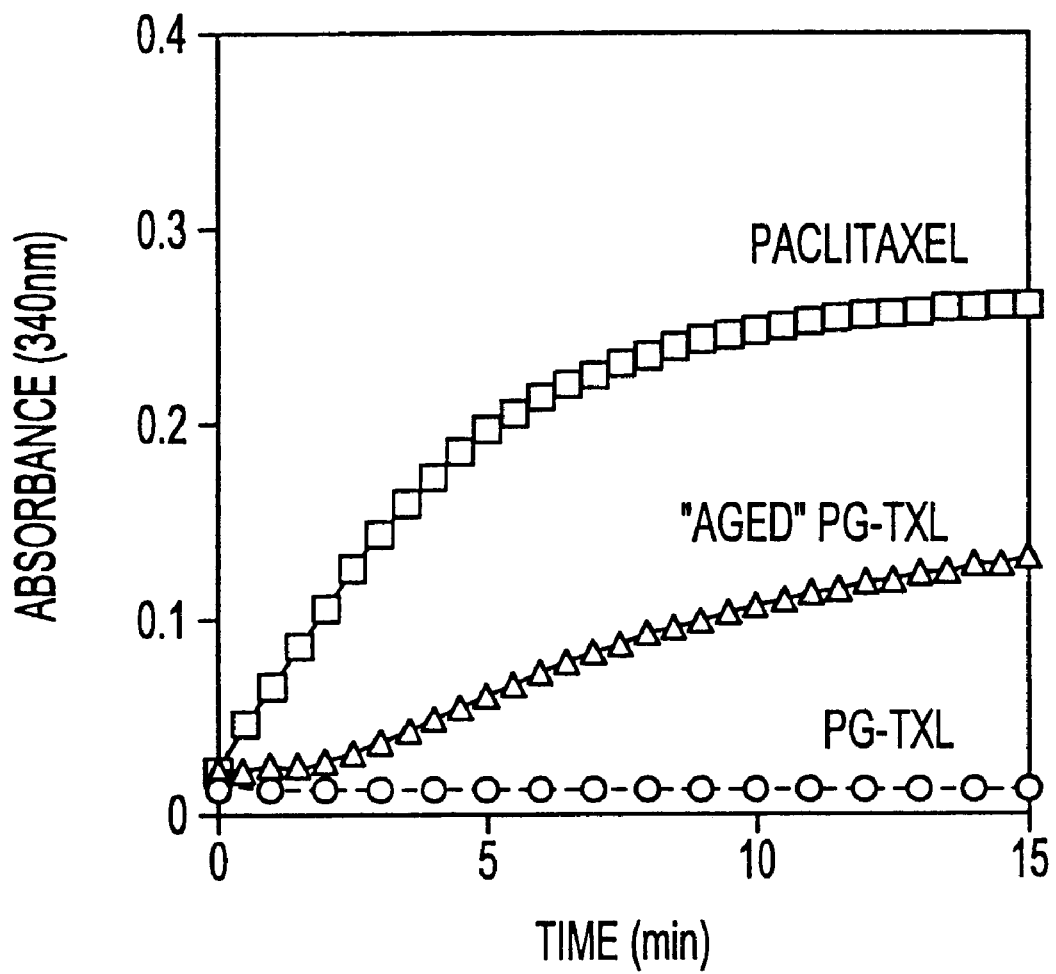

FIG. 10. Tubulin polymerization assays performed at 32° C. in the presence of 1.0 mM GTP and 1.0 mg/ml of tubulin. -□- represents paclitaxel (1.0 μM), -Δ- represents PG-TXL (10 μM equivalent paclitaxel) incubated in PBS (pH 7.4) at 37° C. for 3 days, -○- represents freshly dissolved PG-TXL.

Figure 11:
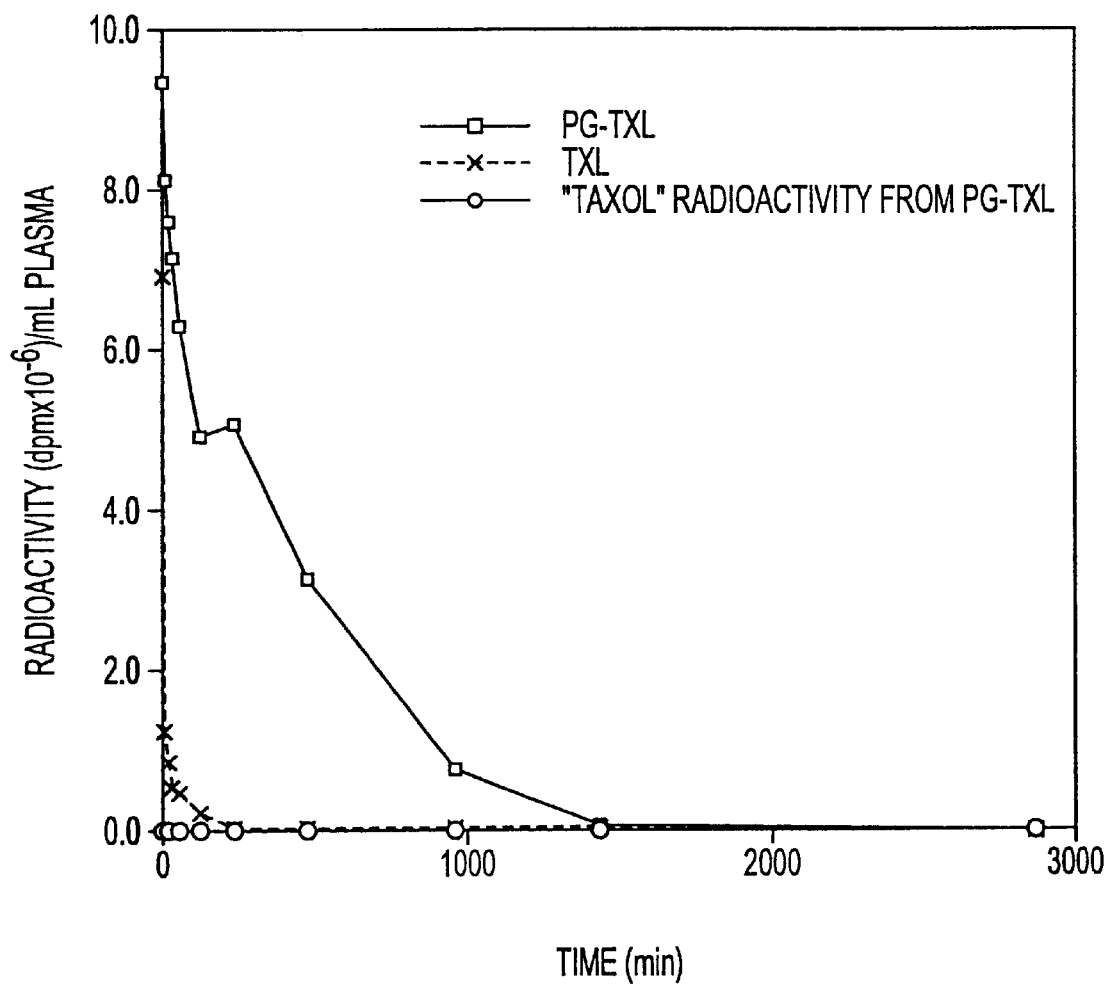

FIG. 11. Plasma clearance of radioactivity following an i.v. injection of PG[$^3$H]paclitaxel and [$^3$H]paclitaxel in C3Hf/Kam mice. -□- represents PG-TXL radioactivity after injection of 6 μCi of radiolabeled PG-[$^3$H]paclitaxel (20 mg equivalent paclitaxel/kg), -x- represents paclitaxel radioactivity after injection of 6 μCi of radiolabeled [$^3$H]paclitaxel (20 mg equivalent paclitaxel/kg), -○- represents "Paclitaxel" radioactivity released from injected PG-[$^3$H]paclitaxel.

Figure 12A:
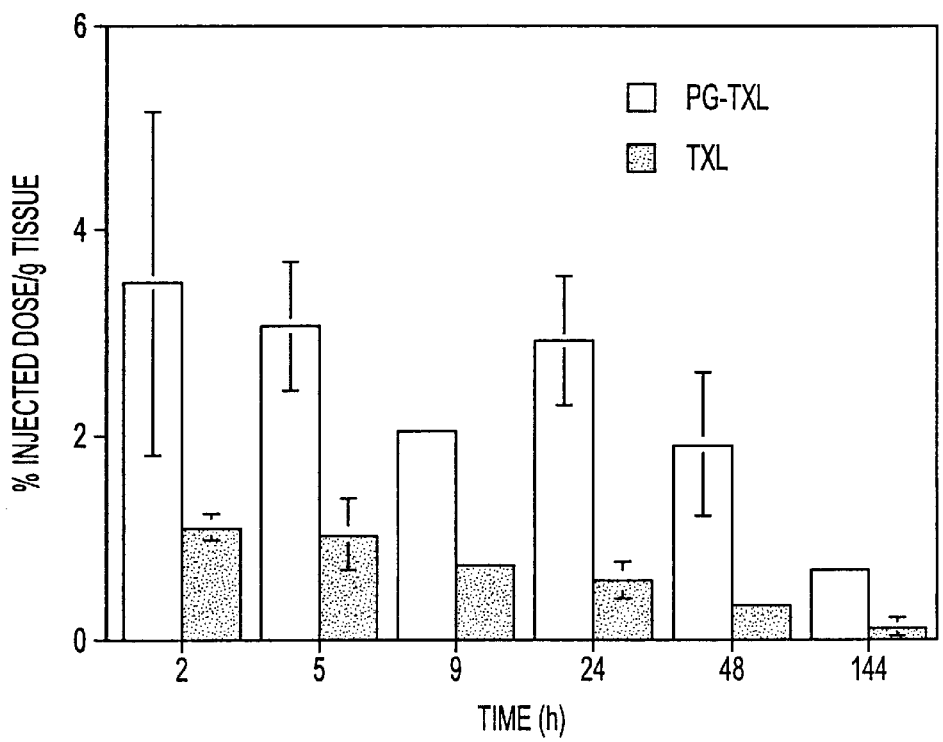

FIG. 12A. Time-dependent OCA-1 tumor content of radioactivity following injection of either PG-[$^3$H]paclitaxel and [$^3$H]paclitaxel into mice. Open bars represents PG-TXL radioactivity after injection of 6 μCi of radiolabeled PG-[$^3$H]paclitaxel (20 mg equivalent paclitaxel/kg), filled bars represents paclitaxel radioactivity after injection of 6 μCi of radiolabeled [$^3$H]paclitaxel (20 mg equivalent paclitaxel/kg).

Figure 12B:
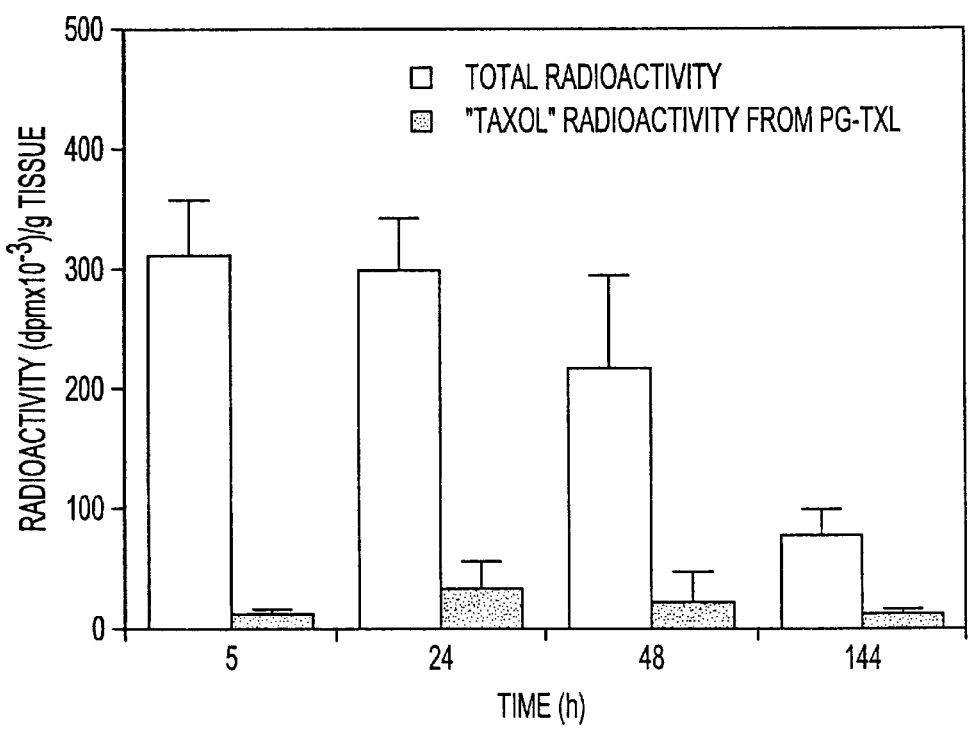

FIG. 12B. Conversion of PG-[$^3$H]paclitaxel to [$^3$H] paclitaxel within OCA-1 tumor. Total radioactivity measured after injection of 6 μCi of radiolabeled PG-[$^3$H] paclitaxel is shown in open bars, "Paclitaxel" derived radioactivity released from injected PG[$^3$H]paclitaxel is shown in solid bars.

Figure 13:
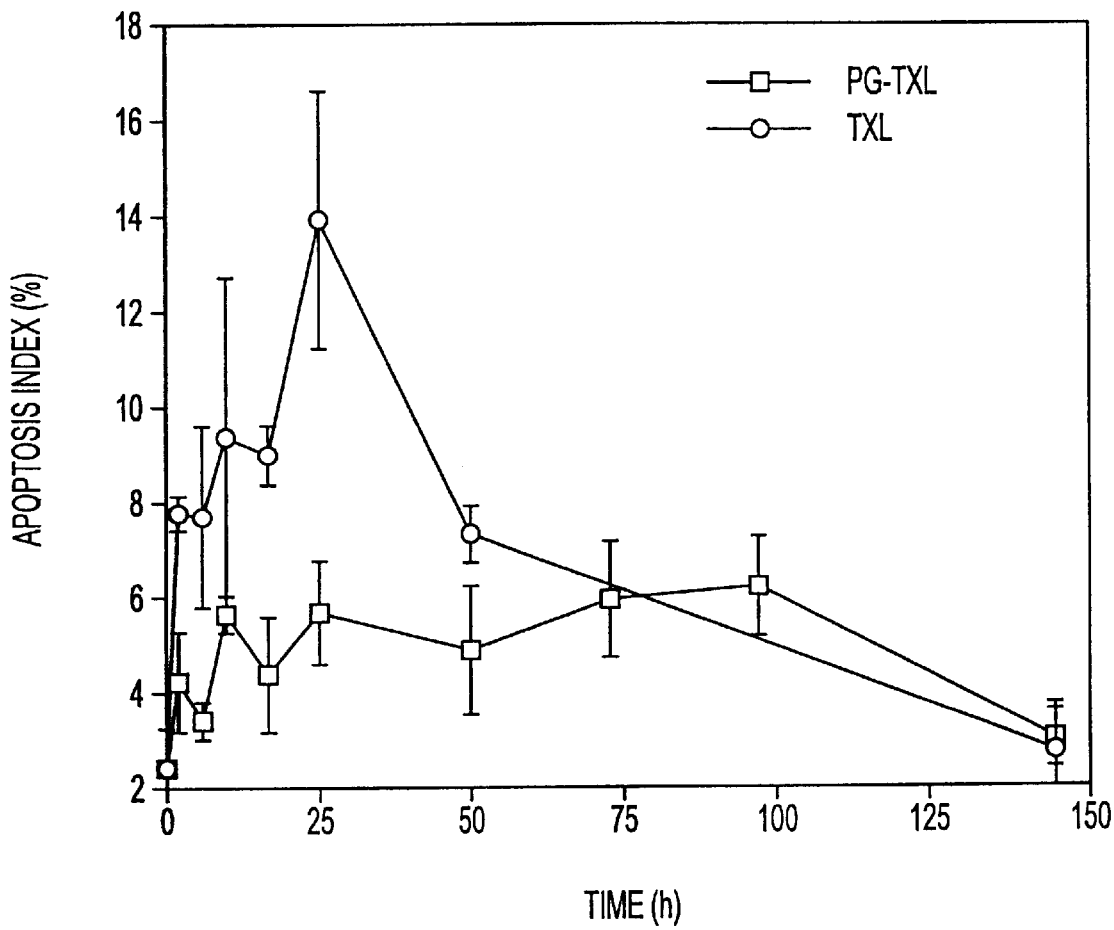

FIG. 13. Kinetics of apoptosis in OCA-1 tumors after a single i.v. dose of 160 mg equiv. paclitaxel/kg of PG-TXL (MTD) and 80 mg/kg paclitaxel (MTD), -□- represents the response to a single i.v. dose of PG-TXL (160 mg equiv. paclitaxel/kg MTD), -○- represents response to paclitaxel (80 mg paclitaxel/kg MTD).

Figure 14:
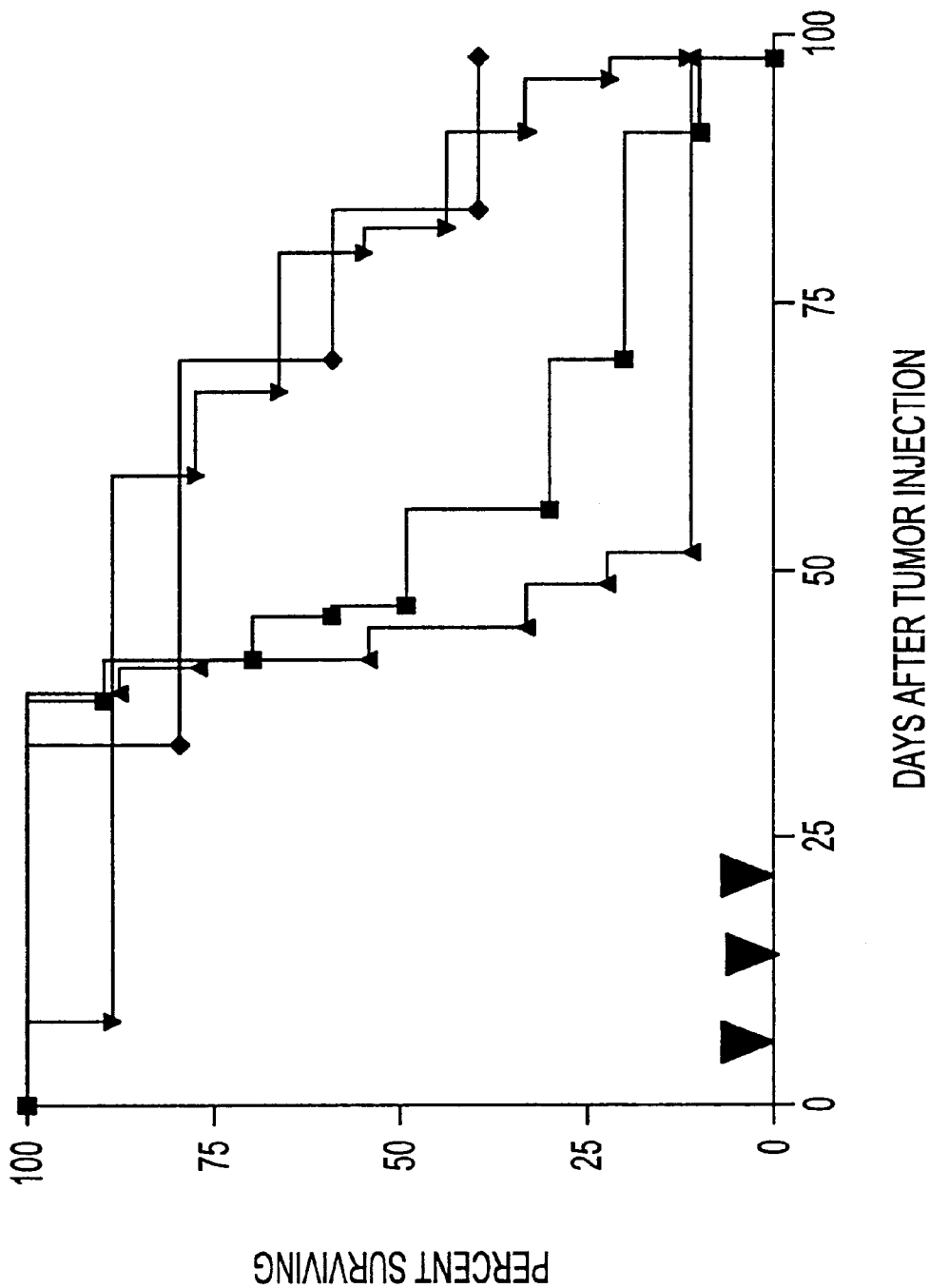

FIG. 14. Survival of nude mice with human ovarian cancer cells (SKOV3ipl) treated with PG-TXL. Five days after tumor injection, the mice were injected i.v. with the PG-paclitaxel (PG-TXL), or PG control. Injections of PG-TXL were administered every seven days (▼) in the 120 mg/kg group, but not the 160 mg/kg group. -■- represents untreated mice. -▼- represents the response to multiple i.v. doses of PG. -▼- represents the response to an i.v. dose of PG-TXL (120 mg equiv. paclitaxel/kg), -♦- represents the response to an i.v. dose of PG-TXL (160 mg equiv. paclitaxel/kg).

Figure 15:
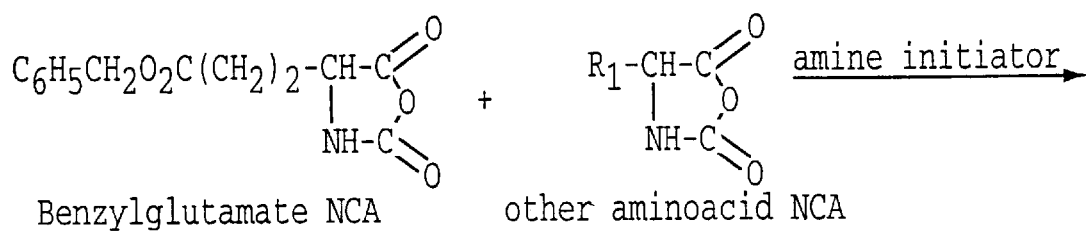
Figure 15:
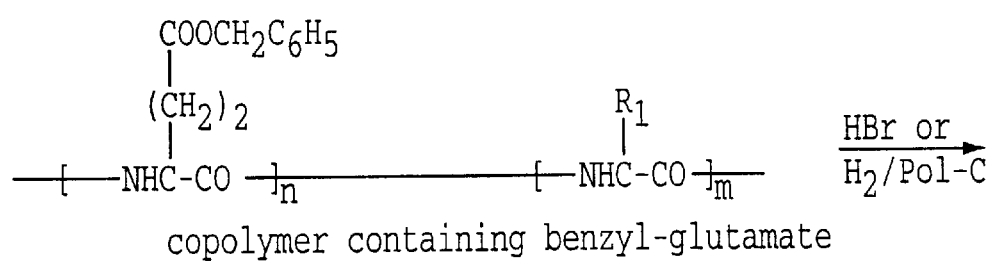
Figure 15:
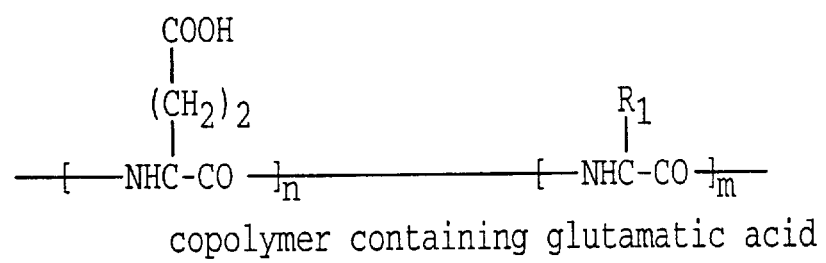

FIG. 15. Chemical structure and reaction scheme for production of glutamic acid containing polyamino acids.

DETAILED DESCRIPTION OF THE PREFERRED EMBODIMENTS

The present invention arises from the discovery of novel, water soluble formulations of paclitaxel and docetaxel, and the surprising efficacy of these formulations against tumor cells in vivo. Poly (1-glutamic acid) conjugated paclitaxel (PG-TXL) administered to mice bearing ovarian carcinoma (OCA-1) caused significant tumor growth delay as compared to the same dose of paclitaxel without PG. Mice treated with paclitaxel alone or with a combination of free paclitaxel and PG showed delayed tumor growth initially, but tumors regrew to levels comparable to an untreated control group after ten days. Moreover, at the maximum tolerated dose (MTD) of the PG-TXL conjugate, (160 mg equiv. paclitaxel/kg), the growth of tumors was completely suppressed, the tumors shrank, and mice observed for two months following treatment remained tumor free (MTD: defined as the maximal dose that produced 15% or less body weight loss within two wk after a single i.v. injection). In a parallel study, the antitumor activity of PG-TXL in rats with rat mammary adenocarcinoma (13762F) was examined. Again, complete tumor eradication at 40–60 mg equiv. paclitaxel/kg of PG-TXL was observed. These surprising results demonstrate that the polymer-drug conjugate, PGTXL, successfully eradicates well established solid tumors in both mice and rats after a single intravenous injection.

In addition to the remarkable antitumor (breast, ovarian, etc.) data in syngeneic mice, good activity of PG-TXL against human breast cancer (MDA-435) and ovarian cancer (SKOV3ip1) in nude mice has recently been observed. Nude mice are special animals with incomplete immune systems in which human tumors can grow.

The data presented herein have led the present inventors to conclude that PG-TXL is a novel species of taxane that is pharmacologically distinct from previous paclitaxel or Taxol™ preparations. For example, the distribution of PG-TXL within plasma is distinct from free paclitaxel. While paclitaxel remains in the plasma of mice for an extremely short time, PG-TXL appears to remain for a much longer period. This is contemplated to offer a distinct advantage in that prolonged exposure of tumors to the drug may result in an enhanced response. The rate of conversion of PG-TXL to paclitaxel is slow, with less than 1% of the radioactivity from radiolabeled PG-TXL being recovered as radioactive paclitaxel within 48 h after injection of the paclitaxel-polymer complex. This finding suggests that the novel drug, PG-TXL, may produce death within tumor cells in a manner which is not simply due to the gradual release of paclitaxel itself.

Further evidence of the novelty of PG-TXL is that relatively high levels of radioactivity from radiolabeled PG-TXL appear in tumor tissue shortly after injection. However, only small amounts of radioactivity within tumor tissue are due to the release of free paclitaxel. Furthermore, the percent of radioactivity within tumor tissue due to paclitaxel itself does not appreciably increase with time suggesting again that PG-TXL is a minimal prodrug for the gradual release of paclitaxel. Uptake of PG-TXL versus paclitaxel has also been studied in a specialized human colon adenocarcinoma cell transport system. While radioactivity associated with radiolabeled PG-TXL readily gained entry into cells, only 10% of it was due to free paclitaxel. These data parallel that which was found in studies of tissue distribution and again suggest that there are several mechanisms or ways in which PG-TXL may lead to the death of cancer cells which are different from those for paclitaxel.

In another study, it was discovered that freshly prepared PG-TXL does not support the growth of paclitaxel-dependent cell lines suggesting that free paclitaxel is only slowly released from the polymer-paclitaxel complex and that the polymerpaclitaxel complex itself is not behaving pharmacologically as "Taxol™". Aging will promote the degradation of PG-TXL and does increase the relative ability of the resulting material to support the growth of paclitaxel-dependent cells, but to a lesser extent than compared to free paclitaxel.

Recent analyses of tumor tissues from mice treated with paclitaxel suggests that, as expected, this drug results in the formation of many apoptotic bodies within the tumor itself. Apoptosis is a mechanism in which cells commit self-induced death or programmed cell death, a natural process used by an organism in wound healing and tissue remodeling. Tumors from mice treated with PG-TXL had far fewer apoptotic bodies compared to free paclitaxel but had an increased incidence of tumor necrosis and edema suggesting that paclitaxel and PG-TXL may result in tumor cell death by two distinctly different pathways.

These studies, and those described in the specific examples, demonstrate that PG-TXL is a new taxane which is not only extremely active against breast and ovarian cancers, and appears to have limited side affects. It is now clear that the polymer conjugation of paclitaxel results in a compound (PG-TXL) that has novel and greater over-all antitumor activity.

Another aspect of the present invention is the inclusion of molecules in the polymeric composition that are effective to target the therapeutic composition to a disease or tumor site or to a particular organ or tissue. Many of such targeting molecules are known in the art and may be conjugated to the water soluble anti-tumor compositions of the present invention. Examples of such molecules or agents would include, but not be limited to antibodies such as anti-tumor antibodies; anti-cell receptor antibodies; tissue specific antibodies; hormonal agents such as octreotide, estradiol and tamoxifen; growth factors; cell surface receptor ligands; enzymes; hypoxic agents such as misonidazole and erythronitroimidazole; and antiangiogenic agents.

Another composition of the present invention is DTPA-paclitaxel, also shown herein to be as effective as paclitaxel in an in vitro antitumor potency assay using a B16 melanoma cell line. DTPA-paclitaxel did not show any significant difference in antitumor effect as compared to paclitaxel against an MCa-4 mammary tumor at a dose of 40 mg/kg body weight in a single injection. Furthermore, $^{111}$Indium labeled DTPA-paclitaxel was shown to accumulate in the MCa-4 tumor as demonstrated by gammascintigraphy, demonstrating that the chelator conjugated anti-tumor drugs of the present invention are useful and effective for tumor imaging.

The novel compounds and methods of the present invention provide significant advances over prior methods and compositions, as the water-soluble paclitaxels are projected to improve the efficacy of paclitaxel-based anti-cancer therapy, by providing water soluble and controlled release paclitaxel derived compositions that also have different antitumor properties than unmodified paclitaxel. Such compositions eliminate the need for solvents that are associated with side effects seen with prior paclitaxel compositions. In addition, radiolabeled paclitaxel, which is shown to retain anti-tumor activity, will also be useful in the imaging of tumors. Further, the present invention allows one to determine whether a paclitaxel will be taken up by a particular tumor by scintigraphy, single photon emission computer tomography (SPECT) or positron emission tomography (PET). This determination may then be used to predict the efficacy of an anti-cancer treatment. This information may be helpful in guiding the practitioner in the selection of patients to undergo chelator-paclitaxel therapy.

The paclitaxel may be rendered water-soluble in many ways: i.e. by conjugating paclitaxel to water-soluble polymers which serve as drug carriers, and by derivatizing the antitumor drug with water soluble chelating agents. The latter approach also provides an opportunity for labeling with radionuclides (e.g., $^{111}$In, $^{90}$Y, $^{166}$Ho, $^{68}$Ga, $^{99m}$Tc) for nuclear imaging and/or for radiotherapy studies. The structures of paclitaxel, polyethylene glycol-paclitaxel (PEG-paclitaxel), poly-glutamic acid-paclitaxel conjugate (PG-TXL) and diethylenetriaminepentaacetic acid-paclitaxel (DTPA-paclitaxel) are shown in FIG. 1.

In certain embodiments of the present invention, DTPA-paclitaxel or other paclitaxel-chelating agent conjugates, such as EDTA-paclitaxel, DTTP-paclitaxel, or DOTA-paclitaxel, for example, may be prepared in the form of water-soluble salts (sodium salt, potassium salt, tetrabutylammonium salt, calcium salt, ferric salt, etc.). These salts will be useful as therapeutic agents for tumor treatment. Secondly, DTPA-paclitaxel or other paclitaxel-chelating agents will be useful as diagnostic agents which when labeled with radionuclides such as $^{111}$In or $^{99m}$TC, may be used as radiotracers to detect certain tumors in combination with nuclear imaging techniques. It is understood that in addition to paclitaxel (Taxol™) and docetaxel (Taxotere), other taxane derivatives may be adapted for use in the compositions and methods of the present invention and that all such compositions and methods would be encompassed by the present invention.

As modifications and changes may be made in the structure of the water soluble polymer such as a water soluble polyamino acid, or a water soluble metal chelator, of the present invention and still obtain molecules having like or otherwise desirable characteristics, such "biologically functional equivalents" or "functional equivalents" are also encompassed within the present invention.

For example, one of skill in the art will recognize that certain amino acids may be substituted for other amino acids in a polyamino acid structure, including water soluble amino acid polymers such as poly-glutamic acid, poly-aspartic acid, or poly-lysine, without appreciable loss of interactive binding capacity with structures such as, for example, a chemotherapeutic and/or antiangiogenic drug, such as paclitaxel or docetaxel, or such like. Additionally, amino acid substitutions in a water soluble polyamino acid conjugated to a chemotherapeutic and/or antiangiogenic drug, such as paclitaxel or docetaxel, or such like, as exemplified by but not limited to PG-TXL, may be made and still maintain part or all of the novel pharmacological properties disclosed herein. Since it is the interactive capacity and nature of a protein that defines that protein's biological functional activity, certain amino acid sequence substitutions can be made in a polyamino acid sequence and nevertheless obtain a polyamino acid with like (agonistic) properties. It is thus contemplated by the inventors that various changes may be made in the sequence of the water soluble polyamino acids of a drug conjugate, such as, but not limited to PG-TXL, without appreciable loss of their biological utility or activity.

In terms of functional equivalents, it is well understood by the skilled artisan that, inherent in the definition of a "biologically functional equivalent of a water soluble polyamino acid," is the concept that there is a limit to the number of changes that may be made within a portion of the molecule and still result in a molecule with an acceptable level of equivalent biological activity. Biologically functional equivalent of a water soluble polyamino acids, are thus defined herein as those water soluble polyamino acids in which certain, not most or all, of the amino acids may be substituted by non-water soluble amino acids, whether natural, unusual, or chemically modified.

In particular, where shorter length water soluble polyamino acids are concerned, it is contemplated that fewer amino acids should be made within the given peptide. Longer domains may have an intermediate number of changes. The longest water soluble polyamino acid chains, as described herein, will have the most tolerance for a larger number of changes. Of course, a plurality of distinct water soluble polyamino acids, such as but not limited to poly glutamic acid, poly aspartic acid, or poly-lysine, with different substitutions may easily be made and used in accordance with the invention.

It is also well understood that where certain residues are shown to be particularly important to the biological or structural properties of a polyamino acid, such residues may not generally be exchanged. In this manner, functional equivalents are defined herein as those water soluble polyamino acids which maintain a substantial amount of their native biological activity.

Amino acid substitutions are generally based on the relative similarity of the amino acid side-chain substituents, for example, their hydrophobicity, hydrophilicity, charge, size, and the like. An analysis of the size, shape and type of the amino acid sidechain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein, and correspondingly a polyamino acid, is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); senne (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. Hence, in reference to hydrophilicity, arginine, lysine, aspartic acid, and glutamic acid are defined herein as biologically functional equivalents, particularly in water soluble amino acid polymers.

In addition to the water soluble polyamino acid-chemotherapeutic and/or antiangiogenic drug compounds described herein, such as paclitaxel or docetaxel conjugated to a water soluble amino acid, or such like, as exemplified by, but not limited to PG-TXL compounds described herein, the inventors also contemplate that other sterically similar compounds may be formulated to mimic the key portions of the water soluble polyamino acid structure. Such compounds, which may be termed peptidomimetics, may be used in the same manner as the peptides of the invention and hence are also functional equivalents.

Certain mimetics that mimic elements of protein secondary structure are described in Johnson et al. (1993). The underlying rationale behind the use of peptide mimetics is that the peptide backbone of proteins, including polyamino acids, exists chiefly to orientate amino acid side chains in such a way as to facilitate molecular interactions, such as those of antibody and antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of receptor modeling is now well known, and by such methods a chemical that binds to water soluble polyamino acids can be designed and then synthesized. It will be understood that all such sterically designed constructs fall within the scope of the present invention.

In addition to the 20 "standard" amino acids provided through the genetic code, modified or unusual amino acids are also contemplated for use in the present invention. A table of exemplary, but not limiting, modified or unusual amino acids is provided herein below.

TABLE 1

Modified and Unusual Amino Acids

| Abbr. | Amino Acid |
|---|---|
| Aad | 2-Aminoadipic acid |
| bAad | 3-Aminoadipic acid |
| bAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| bAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| aHyl | allo-Hydroxylysine |
| 3Hyp | 3-Hydroxyproline |
| 4Hyp | 4-Hydroxyproline |
| Ide | Isodesmosine |
| alle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornthine |

Toxicity studies, pharmacokinetics and tissue distribution of DTPA-paclitaxel have shown that in mice the LD50 (50% lethal dose) of DPTA-paclitaxel observed with a single dose intravenous (iv) injection is about 110 mg/kg body weight. Direct comparison with paclitaxel is difficult to make because of the dose-volume constraints imposed by limited solubility of paclitaxel and vehicle toxicity associated with iv administration. However, in light of the present disclosure, one skilled in the art of chemotherapy would determine the effective and maximum tolerated doses (MTD) in a clinical study for use in human subjects.

In certain embodiments of the invention, a stent coated with the polymerpaclitaxel conjugates may be used to prevent restenosis, the closure of arteries following balloon angioplasty. Recent results in clinical trials using balloon-expandable stents in coronary angioplasty have shown a significant benefit in patency and the reduction of restenosis compared to standard balloon angioplasty (Serruys et al., 1994). According to the response-to-injury hypothesis, neointima formation is associated with increased cell proliferation. Currently, popular opinion holds that the critical process leading to vascular lesions in both spontaneous and accelerated atherosclerosis is smooth muscle cell (SMC) proliferation (Phillips-Hughes and Kandarpa, 1996). Since SMC phenotypic proliferation after arterial injury mimics that of neoplastic cells, it is possible that anticancer drugs may be useful to prevent neointimal SMC accumulation. Stents coated with polymer-linked anti-proliferative agents that are capable of releasing these agents over a prolonged period of time with sufficient concentration will thus prevent ingrowth of hyperplastic intima and media into the lumen thereby reducing restenosis.

Because paclitaxel has been shown to suppress collagen induced arthritis in a mouse model (Oliver et al. 1994), the formulations of the present invention are also contemplated to be useful in the treatment of autoimmune and/or inflammatory diseases such as rheumatoid arthritis. Paclitaxel binding to tubulin shifts the equilibrium to stable microtubule polymers and makes this drug a strong inhibitor of eukaryotic cell replication by blocking cells in the late G2 mitotic stage. Several mechanisms may be involved in arthritis suppression by paclitaxel. For example, paclitaxel's phase specific cytotoxic effects may affect rapidly proliferating inflammatory cells, and furthermore paclitaxel inhibits cell mitosis, migration, chemotaxis, intracellular transport and neutrophil $H_2O_2$ production. In addition, paclitaxel may have antiangiogenic activity by blocking coordinated endothelial cell migration (Oliver et al. 1994). Therefore, the water soluble polyamino acids conjugated paclitaxel of the present invention are contemplated to be useful in the treatment of rheumatoid arthritis. The polymer conjugated formulation disclosed herein would also offer the advantages of controlled release of the drug and greater solubility. It is also an aspect of the treatment of arthritis that the formulations may be injected or implanted directly into the affected joint areas.

The pharmaceutical preparations of paclitaxel or docetaxel suitable for injectable use include sterile aqueous solutions or dispersions and sterile powders for the preparation of sterile injectable solutions or dispersions. In all cases the form must be sterile and must be fluid for injection. It must be stable under the conditions of manufacture and storage and must be preserved against the contaminating action of microorganisms, such as bacteria and fungi. The carrier may be a solvent or dispersion medium containing, for example, water, ethanol, polyol (for example, glycerol, propylene glycol and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents and isotonic agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" also refers to molecular entities and compositions that do not produce an allergic or similar untoward reaction when administered to an animal or a human.

For parenteral administration in an aqueous solution, for example, the solution should be suitably buffered if necessary and the liquid diluent first rendered isotonic with sufficient saline or glucose. These particular aqueous solutions are especially suitable for intravenous and intraperitoneal administration. In this connection, sterile aqueous media which can be employed will be known to those of skill in the art in light of the present disclosure.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Poly-Glutamic Acid-Paclitaxel (PG-TXL)

The present example concerns a first study involving the conjugation of paclitaxel to a water-soluble polymer, poly (1-glutamic acid) (PG) and the efficacy of the preparation against a variety of tumors in mice and rats. The potential of water-soluble polymers used as drug carriers is well established (Kopecek, 1990; Maeda and Matsumura, 1989).

Synthesis of Poly-Glutamic Acid-Paclitaxel (PG-TXL)

PG was selected as a carrier for paclitaxel because it can be readily degraded by lysosomal enzymes, is stable in plasma and contains sufficient functional groups for drug attachment. Several antitumor drugs, including Adriamycin (Van Heeswijk et al., 1985; Hoes et al., 1985), cyclophosphamide (Hirano et al., 1979), Ara-C (Kato et al., 1984) and melphalan (Morimoto et al., 1984) have been conjugated to PG. However, poly-aspartic acid may be conjugated to anti-tumor drugs using the reaction scheme described herein for PG-TXL.

Figure 1A:
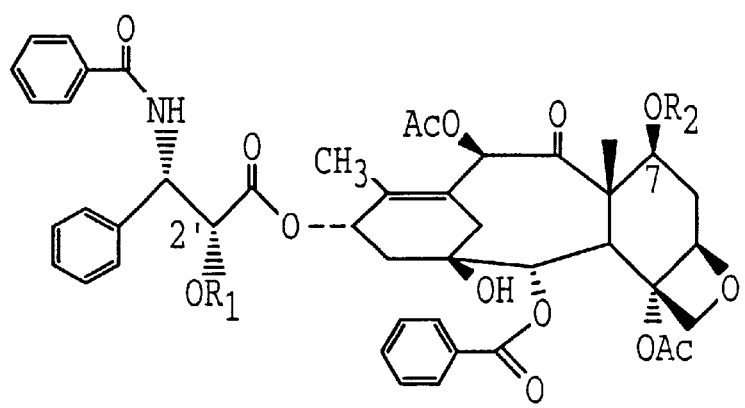
FIG. 1A. Chemical structure of paclitaxel, PEG-paclitaxel and DTPA-paclitaxel.
Figure 1A:
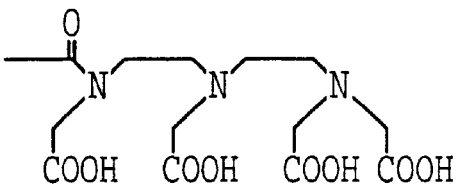
Figure 1A:
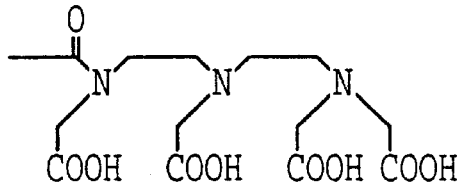
Figure 1B:
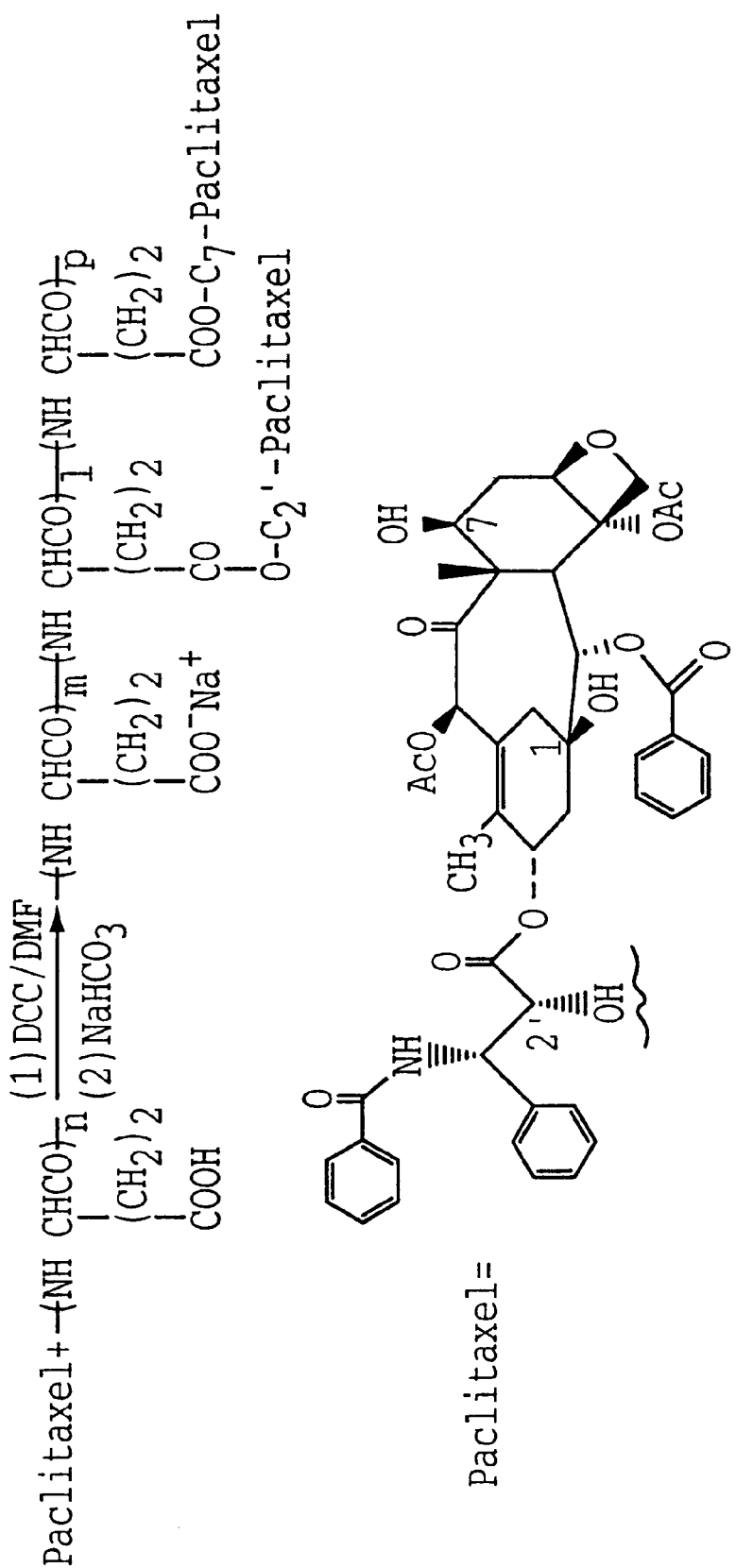
FIG. 1B. Chemical structure and reaction scheme for production of PG-TXL.

The reaction scheme is presented in FIG. 1B. Poly(1-glutamic acid) (PG) sodium salt was obtained from Sigma (St. Louis, Mo.). The polymer by viscosity had a molecular weight of 36,200, and number-average molecular weight ($M_n$) of 24,000 as determined by low-angle laser light scattering (LALLS). Lot-specific polydispersity ($M_w/M_n$) was 1.15 where $M_w$ is weight-average molecular weight. PG sodium salt (MW 34 K, Sigma, 0.35 g) was first convened to PG in its proton form. The pH of the aqueous PG sodium salt solution was adjusted to 2.0 using 0.2 M HCl. The precipitate was collected, dialyzed against distilled water, and lyophilized to yield 0.29 g PG.

To a solution of PG (75 mg, repeating unit FW 170, 0.44 mmol) in dry N,N-dimethylformamide (DMF) (1.5 mL) was added 22 mg paclitaxel (0.026 mmol, molar ratio PG/paclitaxel=17), 15 mg dicyclohexyfcarbodiimide (DCC) (0.073 mmol) and trace amount of dimethylaminopyridine (DMAP). Paclitaxel was supplied by Hande Tech (Houston, Tex.), and the purity was 99% and higher as confirmed by HPLC assay.

The reaction was allowed to proceed at room temperature for 12–18 h. Thin layer chromatography (TLC, silica) showed complete conversion of paclitaxel (Rf=0.55) to polymer conjugate (Rf=0, CHCl3/MeOH=10:1). To stop the reaction, the mixture was poured into chloroform. The resulting precipitate was collected and dried in vacuum to yield 70 mg polymer-drug conjugate. By changing the weight ratio of paclitaxel to PG in the starting materials, polymeric conjugates of various paclitaxel concentrations can be synthesized.

The sodium salt of PG-TXL conjugate was obtained by dissolving the product in 1.0 M NaHCO3. The aqueous solution of PG-TXL was dialyzed against distilled water (MWCO 10,000) to remove low molecular weight contaminants and excess NaHCO3 salt. Lyophilization of the dialysate yielded 98 mg of product as a white powder. The paclitaxel content in this polymeric conjugate as determined by UV was 20–22% (w/w). Yield: 98% (conversion to polymer bound paclitaxel, UV). Solubility in water>20 mg paclitaxel/ml. A similar method can be used to synthesize PG-TXL with higher paclitaxel content (up to 35%) by simply increasing the ratio of paclitaxel to PG used.

Characterization of Poly-Glutamic Acid-Paclitaxel (PG-TXL)

Ultraviolet spectra were obtained on a Beckman DU-70 spectrophotometer, using the same concentration of PG aqueous solution as reference. PG-TXL showed characteristic paclitaxel absorption with $\lambda_{max}$ shifts from 228 to 230 nm. The concentration of paclitaxel in PG-TXL conjugate was estimated based on standard curve generated with known concentrations of paclitaxel in methanol at absorption of 228 nm assuming that the polymer conjugate in water at 230 nm and the free drug in methanol at 228 nm have the same molar extinction and both follow Lambert Beer's law.

$^1$H-NMR spectra were recorded with GE model GN 500 (500 MHz) spectrometer in $D_2O$. Both the PG moieties and the paclitaxel moieties were discernible. The couplings of polymer conjugated paclitaxel are too poorly resolved to be measured with sufficient accuracy. Resonances at 7.75 to 7.36 ppm are attributable to aromatic components of paclitaxel resonances at 6.38 ppm ($C_{10}$—H), 5.97 ppm ($C_3$—H), 5.63 ppm ($C_2$'—H, d), 5.55–5.36 ppm ($C_3$'—H and $C_2$—H, m), 5.10 ppm ($C_5$—H), 4.39 ppm ($C_7$—H), 4.10 ($C_{20}$—H), 1.97 ppm ($OCOCH_3$), and 1.18–1.20 ppm (C $CH_3$) are tentatively assigned to aliphatic components of paclitaxel. Other resonances were obscured by the resonances of PG. PG resonances at 4.27 ppm (H-α), 2.21 ppm (H-γ), and 2.04 ppm (H-β) are in accordance with pure PG spectrum. Although a peak at 5.63 ppm could be tentatively assigned to the C-2' proton of the C-2' ester, the C-2' proton of unsubstituted paclitaxel at 4.78 ppm was also present, suggesting that the resulting conjugate may contain paclitaxel substitutions at both the C-2' and C-7 positions. A 100 mg/ml solution of the conjugate produces a clear, viscous, yet flowable liquid. This procedure consistently produces PG-TXL conjugate containing 20% of paclitaxel by weight, i.e., approximately 7 paclitaxel molecules are bound to each polymer chain.

Gel Permeation Chromatography Studies of Poly-Glutamic Acid-Paclitaxel (PGTXL)

The relative molecular weight of PG-TXL was characterized by gel permeation chromatography (GPC). The GPC system consisted of two LDC model III pumps coupled with LDC gradient master, a PL gel GPC column, and a Waters 990 photodiode array detector. The elutant (DMF) was run at 1.0 ml/min with ultraviolet (UV) detection set at 270 mm. For PG-TXL sodium salt, a TSK-gel column suitable for analysis of water-soluble polymer was used, and the system was eluted with 0.2 mM PBS (pH 6.8) at 1.0 ml/min. Conjugation of paclitaxel to PG resulted in an increase in the molecular weight of PG-TXL, as indicated by the shift of retention time from 6.4 mm for PG to 5.0 mm for PG-TXL conjugate. The crude product contained small molecular weight contaminants (retention time 8.0 to 10.0 mm, and 11.3 min), which can be effectively removed by convening PG-TXL to its sodium salt, followed by dialysis.

Hydrolytic Degradation of a Poly-Glutamic Acid-Paclitaxel (PG-TXL) Conjugate

Figure 6A:
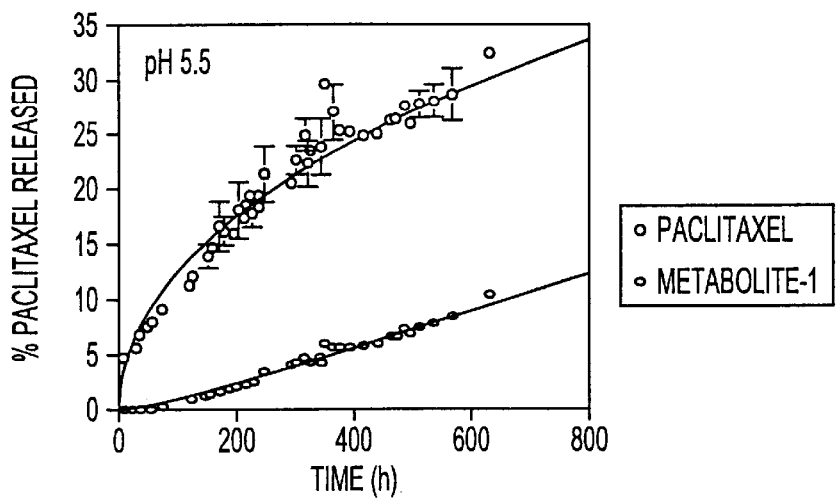
FIG. 6. Hydrolytic degradation of PG-TXL as determined in PBS as a function of time at different pH levels. -◊- represents percent paclitaxel released, -O- represents metabolite-1 produced.
Figure 6B:
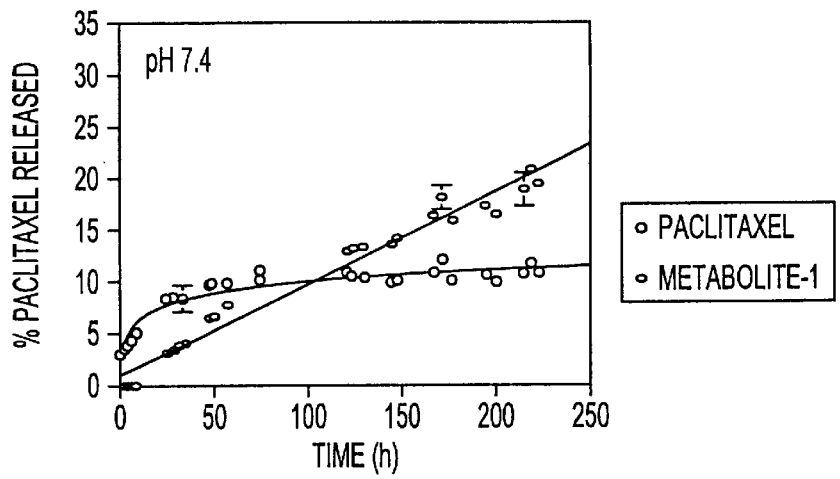
Figure 6C:
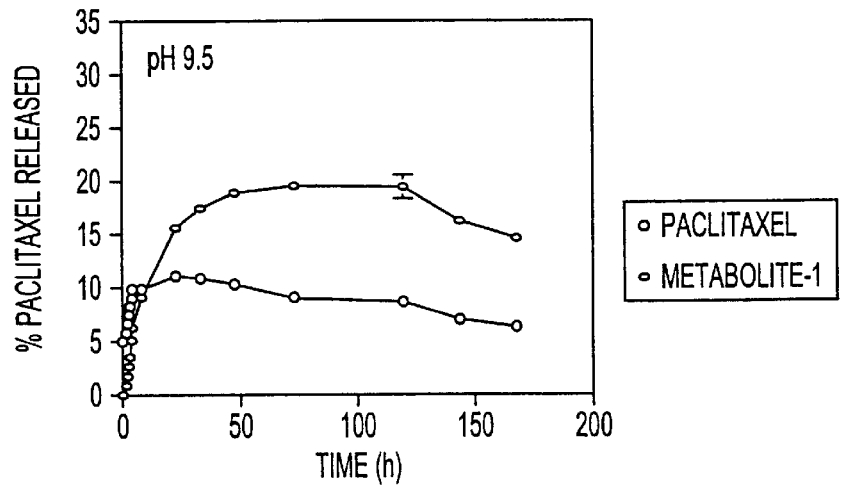

To gain insight on the release kinetics of paclitaxel and related molecular species from PG-TXL, the hydrolytic stability of PG-TXL was tested in PBS at various pH. High performance liquid chromatography (HPLC) revealed that incubation of PG-TXL in PBS solutions produced paclitaxel and several other species including one that is more hydrophobic than paclitaxel (metabolite 1). The fact that these species all were derived from paclitaxel was confirmed through similar degradation studies using PG-[3H]TXL. Based on its retention time on HPLC, metabolite-1 is probably 7-epipaclitaxel, a biologically active isomer of paclitaxel. In fact, the amount of metabolite 1 recovered in PBS surpassed that of paclitaxel after 5 days and 1 day of incubation at pH 7.4 and pH 9.5 respectively (FIG. 6). At pH 5.5 and pH 7.4, the release profiles of metabolite 1 indicated pseudo-zero order kinetics and displayed a delay time varying from 3 days (pH 5.5) to 7 h (pH 7.4), suggesting that metabolite-1 is a secondary product. Apparently, PG-TXL is more stable in acidic solution than in basic solution.

In Vivo Antitumor Activity

All animal work was carried out at the animal facility at M.D. Anderson Cancer Center in accordance with institutional guidelines. C3H/Kam mice were bred and maintained in a pathogen-free facility in the Department of Experimental Radiation Oncology.

The tumor growth delay induced by PG-TXL was measured in mammary ovarian carcinoma (OCA-1) implanted in C3Hf/Kam mice. All tumors were syngeneic to this strain. Solitary tumors were produced in the muscle of the right thigh of female C3H/Kam mice (25–30g) by injecting $5\times10^5$ murine ovarian carcinoma cells (OCA-1), mammary carcinoma (MCa-4), hepatocarcinoma (HCa-I) or fibrous sarcoma (FSa-II). In a parallel study, female Fischer 344 rats (125–150 g) were injected with $1.0\times10^5$ viable 13762F tumor cells in 0.1 ml PBS. Treatments were initiated when the tumors in mice had grown to 500 mm$^3$ (10 mm in diameter), or when the tumors in rats had grown to 2400 mm$^3$ (mean diameter 17 mm).

PG-TXL was disolved in saline (10 mg equivalent paclitaxel/ml), and paclitaxel was dissolved in Cremophor EL® vehicle (6 mg/ml). Data are presented as mean±standard deviation of tumor volumes. In control studies, saline (0.6 ml), Cremophor vehicle [50/50 Cremophor/ethanol diluted with saline (1:4)], PG solution in saline, and paclitaxel plus PG were used. The maximum tolerated dose (MTD) of PG-TXL and paclitaxel in normal female C3HtYKam mice was estimated to be 160 mg/kg and 80 mg/kg respectively. A single dose of PG-TXL in saline or paclitaxel in Cremophor EL vehicle was given in doses varying from 40 to 160 mg equiv. Paclitaxel/kg body weight. Tumor growth was determined daily (FIGS. 7A, 7B, 7C, 7D and 7E) by measuring three orthogonal tumor diameters. Tumor volume was calculated according to formula (A×B×C)/2. Absolute growth delay (AGD) in mice is defined as the time in days for tumors treated with various drugs to grow from 500 to 2,000 mm$^3$ in mice minus the time in days for tumors treated with saline control to grow from 500 to 2,000 mm$^3$. When the tumor size reached 2000 mm$^3$, the tumor growth delay was calculated; the mice were sacrificed when tumors were approximately 2500 mm$^3$. The PG-TXL group were (n=6 and 7), other each group were (n=5). Table 2 summarizes acute toxicity of PG paclitaxel in rats in comparison with paclitaxel/Cremophor. Table 3 summarizes the data concerning the effect of PG-TXL against MCa-4, FSa-II and HCa-I tumors in mice. The data are also summarized in FIG. 7A–FIG. 7E.

TABLE 2

Acute Toxicity of PG-TXL in Fischer Rats*

| Group | Dose (mg/kg) | # of Toxic Death | Body Weight Loss in % | Time at Nadir (days) | Time of Full Recovery (days) |
|---|---|---|---|---|---|
| PG-TXL[a] | 60 | 1/4 | 15.7 | 7 | 14 |
| PG-TXL[a] | 40 | 0/4 | 11.1 | 6 | 11 |
| Paclitaxel[b] | 60 | 1/4 | 16.7 | 6 | 15 |
| Paclitaxel[b] | 40 | 0/3 | 17.9 | 6 | 16 |
| Paclitaxel[b] | 20 | 0/5 | 17.0 | 5 | N/A |

*Drugs were administered intravenously into 13762F tumor-bearing Fischer rats (female, 130 g) in a single injection.
[a]PG-TXL solution was prepared by dissolving the conjugate in saline (8 mg equiv. paclitaxel/ml). The injected volume at 60 mg/kg was 0.975 ml per rat.
[b]Paclitaxel Cremophor solution was prepared by dissolving paclitaxel in a 1:1 mixture of ethyl alcohol and Cremophor (30 mg/ml). This stock solution was further diluted with saline (1:4) before injection. The final concentration of paclitaxel in the solution was 6 mg/ml. The injection volume at 60 mg/ml was 1.3 ml per rat.
[c]PG solution was prepared by dissolving the polymer in saline (22 mg/ml). The injected dose was 0.3 g/kg (1.8 ml per rat), which was equivalent to paclitaxel dose of 60 mg/kg.
[d]Cremophor vehicle was prepared by diluting a mixture of ethyl alcohol and Cremophor (1:1) with saline (1:4).

TABLE 3

The Antitumor Effect of PG-TXL Against Different Types of In vivo Murine Tumors

| Tumor | Drug[a] | Time to Grow[bb] 500–2000 mm$^3$ | AGD[c] | t-test[d] |
|---|---|---|---|---|
| MCa-4 | Saline | 4.8 ± 0.8 (5) | — | — |
| | PG (0.6 g/kg) | 9.3 ± 1.1 (4) | 4.5 | 0.0114 |
| | Cremophor Vehicle | 6.1 ± 0.7 (5) | 1.3 | 0.265 |
| | PG-TXL (40 mg/kg) | 8.6 ± 1.2 (4) | 3.8 | 0.026 |
| | PG-TXL (60 mg/kg) | 14.2 ± 1.1 (5) | 9.4 | 0.0001 |
| | PG-TXL (120 mg/kg) | 44.4 ± 2.9 (5) | 39.6 | <0.0001 |
| | Paclitaxel (40 mg/kg) | 9.0 ± 0.6 (4) | 4.2 | 0.0044 |
| | Paclitaxel (60 mg/kg) | 9.3 ± 0.3 (5) | 4.5 | 0.0006 |
| Fsa-II | Saline | 1.9 ± 0.1 (5) | — | — |
| | PG (0.8 g/kg) | 2.8 ± 0.2 (6) | 0.9 | 0.0043 |
| | Cremophor Vehicle | 2.2 ± 0.2 (6) | 0.3 | 0.122 |
| | PG-TXL (80 mg/kg) | 3.8 ± 0.4 (6) | 1.9 | 0.0016 |
| | PG-TXL (160 mg/kg) | 5.1 ± 0.3 (13) | 3.2 | <0.0001 |
| | Paclitaxel (80 mg/kg) | 4.2 ± 0.3 (6) | 2.3 | 0.0002 |
| | PG + Paclitaxeql | 3.0 ± 0.2 (6) | 1.1 | 0.0008 |

TABLE 3-continued

The Antitumor Effect of PG-TXL Against
Different Types of In vivo Murine Tumors

| Tumor | Drug[a] | Time to Grow[bb] 500–2000 mm$^3$ | AGD[c] | t-test[d] |
|---|---|---|---|---|
| Hca-I | Saline | 7.3 ± 0.3 (5) | — | — |
| | PG (0.8 g/kg) | 7.7 ± 0.4 (4) | 0.4 | 0.417 |
| | Cremophor Vehicle | 6.8 ± 0.8 (5) | −0.5 | 0.539 |
| | PG-TXL (40 mg/kg) | 8.2 ± 0.7 (5) | 0.9 | 0.218 |
| | PG-TXL (80 mg/kg) | 8.6 ± 0.2 (5) | 1.3 | 0.0053 |
| | PG-TXL (160 mg/kg) | 11.0 ± 0.8 (4) | 3.7 | 0.0023 |
| | Paclitaxel (80 mg/kg) | 6.4 ± 0.5 (5) | −0.9 | 0.138 |
| | PG + Paclitaxel | 6.7 ± 0.4 (5) | −0.6 | 0.294 |

[a]Mice bearing 500 mm$^3$ tumors in the right leg were treated with various doses of PG-TXL (40–160 mg equiv. paclitaxel/kg) in saline or paclitaxel in Cremophor vehicle i.v. in a single injection. Control animals were treated with saline (0.6 ml), Cremophor vehicle (0.5 ml), PG solution in saline, or PG g/kg) plus paclitaxel (80 mg/kg).
[b]Tumor growth was determined by daily measurement of three orthogonal diameters with calipers and the volume was calculated as (A × B × C)/2. Shown in brackets are the number of mice used in each group. The time in days to grow from 6 = 500 mm$^3$ to 2000 mm$^3$ are presented mean ± standard deviation.
[c]Absolute growth delay (AGD) defined as the time in days for tumors treated with various drugs to grow from 500 to 2000 mm$^3$ minus the time in days for tumors treated with saline control to grow from 500 to 2000 mm$^3$.
[d]The time in days to grow from 500 to 2000 mm$^3$ were compared for treatment groups and saline group using Student's t-Test. P-values are two-sided and were taken to be significant when less than to equal 0.05.

Two important findings emerged from these studies. First, like paclitaxel, there is an intertumor variability of the antitumor effect of water-soluble PG-TXL. PG-TXL is most effective against MCa-4 and OCA-1 tumors. Second, PG-TXL is more effective than paclitaxel on equivalent mg paclitaxel basis in the case of MCa-4, HCa-I, and on OCA-1 tumors, and is remarkably potent at its maximum tolerated dose (MTD).

In a parallel study, the antitumor activity of PG-TXL in Fischer rats with the well established rat mammary adenocarcinoma 13762F was examined. Femal Fischer 344 rats (125–150 g) were injected with 1.0×10$^5$ viable 13762F tumor cells in 0.1 ml PBS. Once tumors reached a mean volume of 2000 mm$^3$ (mean diameter, 1.6 cm), animals were treated using a similar protocol as described above. Tumor growth was determined daily by measuring three orthogonal tumor diameters. Tumor volume was calculated according to the formula (A×B×C)/2. A single dose of PG-TXL in saline or paclitaxel in a Cremophor EL® vehicle was given in doses varying from 20 to 60 mg equivalent paclitaxel/kg body weight. In control studies, saline, the Cremophor EL® vehicle [50/50 Cremophor/ethanol diluted with saline (1:4)], PG solution in saline and paclitaxel plus PG were used. Again, complete tumor eradication at the MTD of PG-TXL (60 mg equivalent paclitaxel/kg) was observed. PG-TXL given at a lower dose of 40 mg equivalent paclitaxel/kg also resulted in complete tumor regression (FIG. 7B). In contrast, the MTD of paclitaxel in Cremophor EL® was less than 20 mg/kg. Paclitaxel at this dose caused a tumor growth delay (Tumor growth delay is defined as the time in days for tumors treated with the test drugs to grow from 2,000 mm$^3$ to 10,000 mm$^3$ minus the time in days for tumors treated with saline control to grow from 2,000 mm$^3$ to 10,000 mm$^3$) of only 5 days, whereas the same equivalent paclitaxel dose of PG-TXL resulted in a tumor growth delay of 23 days (FIG. 7B).

Studies of Nude Mice Injected with Human Breast Cancer and Treated with PGTXL

Nude mice were injected with 2×106 MDA-435-Lung2 cells (a variant of the MDA-MB-435 human breast cancer cell line) into the mammary fatpad. When the tumors reached 5 mm mean diameter, (27 days after tumor injection), mice were treated with an i.v. injection of PG-TXL or the various controls (see Table 4). Tumor measurements were taken weekly. Tumors that reached 1.5 cm were removed surgically. All mice were killed at 120 days, and remaining tumors removed and weighed. Mice were examined for metastases, and Lungs processed for histology, with single sections of the organs scored for the presence of micrometastases.

TABLE 4

| Treatment | Tumor take[a] | Mean tumor wt(g)[b] | No. tumors regressed[c] | Lung metastases[d] |
|---|---|---|---|---|
| PBS | 5/6 | 1.3 ± 0.24 | — | 4/5 (80%) |
| Cremophor | 9/9 | 1.26 ± 0.67 | — | 4/8 (50%) |
| PGA | 10/10 | 1.13 ± 0.7 | — | 4/7 (57%) |
| Taxol ®/ Cremophor 60 mg/kg | 10/10 | 1.31 ± 0.69 | — | 3/7 (42%) |
| PG-TXL 60 mg/kg | 10/10 | 1.23 ± 0.38 | 2/10 | 5/8 (62.5%) |
| PG-TXL 120 mg/kg | 9/10 | 0.925 ± 0.12 | 4/8 | ¼ (25%) |

[a]Number of mice with 5 mm tumors at time of therapy/number of mice
[b]Mean weight of tumors removed at time of autopsy
[c]Number of tumors that had regressed at time of autopsy
[d]Number of mice with lung metastases (either macroscopic or found in histology preparations)/number of mice with tumors. Some discrepancies between tumor take and number mice with tumors in this column due to sacrifice or deaths of animals for non-related reasons, e.g., developing Staphylococcus abscesses. One mouse in PG-TXL 120 mg group was killed due to extreme weight loss after treatment; otherwise there were no obvious therapy related deaths. Nude mice couldn't tolerate 160 mg/kg equivalent of PG-TXL.

From the results of the study in which a single bolus of PG-conjugated paclitaxel (PG-TXL) was given, at a drug equivalent of 120 mg/kg paclitaxel, it is apparent that the MDA-435 cancer cell line responds to the drug and that this formulation of the drug is much better tolerated than when Cremophor is the vehicle.

In the breast cancer study using MDA-MB-435, only the higher dose of PG-TXL inhibited the growth rate of the mammary fatpad tumors. From the growth curve it was apparent that tumor growth resumed approximately 30 days after the single dose of conjugate. However, the growth curve does not reveal that in the PG-TXL 120 mg/kg group there were a number of tumor regressions. As shown in Table 3, the incidence of lung metastasis in the mice with residual tumors was also reduced. While the numbers of mice in the study are small, they do suggest that the therapy was effective in reducing both local tumor growth and incidence of metastasis.

In this study design it is not possible to distinguish whether a lower incidence of metastasis is due to a reduction of tumor mass of the primary site, or due to a direct effect on any micrometastases that may have already been established at the time of therapy.

In Vivo Therapy of Human Breast Cancer Using Multiple Injections of PG-TXL

To test the effect of multiple injections of PG-TXL, nude mice were injected with 2×10$^6$; MDA-435-Lung 2 cells (a variant of the MDA-MB-435 human breast cancer cell line) into the mammary fatpad. When the tumors reached 5 mm mean diameter, the treatments were started, and repeated at 14 day intervals (day 24, 38, 52) for a total of three injections. Tumor measurements were taken weekly. The mice were killed on day 105 after tumor cell injection, and the tumor weights and incidence of metastasis recorded. The lungs were processed for histology, and single sections scored for the presence of micrometastases. The results are shown in Table 5.

TABLE 5

| Treatment | Tumor take[a] | Mean weight(g)[b] | Tumors regressed[c] | Metastasis[d] |
|---|---|---|---|---|
| None | 4/5 | 1.83 ± 0.15 | — | 4/4 (100%) |
| PG-control | 6/10 | 1.7 ± 0.11 | — | 5/6 (83%) |
| PG-TXL/60 mg | 7/10 | 1.36 ± 0.28 | — | 6/7 (86%) |
| PAG-TXL/120 | 8/10 | 0.97 ± 0.22 p = 0.011 e | — | 2/6 (33%) |

Legend:
[a]Number of mice with 5 mm tumors at the time of therapy/number of mice injected
[b]Mean weight of tumors (±SEM)
[c]Number of tumors that had regressed at the time of autopsy
[d]Number of mice with lung metastases, either macroscopic or microscopic/number of mice with tumors
[d]p value from unpaired t test comparing tumor weight of treated mice with the control PG group.

In Vivo Therapy of Human Ovarian Cancer Using PG-TXL Conjugate

Nude mice were injected i.p. with the human ovarian cancer cell line, SKOV3ipl. Five days after tumor injection, the mice were injected i.v. with the PG-paclitaxel (PGTXL), at concentrations equivalent to 120 mg/kg or 160 mg/kg of paclitaxel. Initially the plan was to repeat these injections at 7-day intervals, but a single injection of the 160 mg/kg dose killed 5 of the 10 mice. Only the 120 mg/kg group received three injections. The study was terminated on day 98, and any surviving mice killed. The results are shown in FIG. 14, and in Table 6.

The median survival values for the groups at present are: untreated=47 days, PC-control=43 days, PG-TXL (120 mg/kg)=83 days, PG-TXL (160 mg/kg)=83 days [note that this does not include the mice that died from the initial toxicity of the drug].

TABLE 6

| Treatment | Tumor take[a] | Median survival (range)[b] | Ascites[c] | Mean vol (ml)[d] |
|---|---|---|---|---|
| None | 10/10 | 56 (38–98) | 8/10 | 2.2 ± 1.6 |
| PG-control | 8/9 | 45 (39–98) | 8/8 | 2.2 ± 1.6 |
| PG-120 | 7/8 | 82 (59–98) | 3/7 | 2.7 ± 1.4 |
| PG-160 | 3/5[e] | 84 (34[f]–98) | 0/3 | |

Legends:
[a]Incidence of tumor/number of mice injected
[b]median survival time in days
[c]incidence of ascites/number of mice with tumor
[d]mean volume (and s.d.) of ascites
[e]these mice only received a single dose of PG-paclitaxel, 160 mg/kg, and does not include the mice that dies within 5 days of the treatment
[f]the mouse that was killed on day 34 had minimal tumor burden, but was paraplegic (possible toxicity?).

The PG-TXL 120 mg/kg significantly extended the survival of the mice with intraperitoneal SKOV3ipl, (a human ovarian cancer cell line which overexpresses HER2/neu), compared with mice injected with PG alone. Multiple doses and/or increasing the dose of conjugate may significantly reduce the tumor incidence in addition to extending survival.

In the nude mice studies above, the growth curves show that although breast cancer growth is checked by paclitaxel, especially with the higher dose conjugated with PG, tumor size continues to increase about a month after the therapy. A second (or third) round of therapy may have caused the tumor growth to plateau, or give more tumor regressions. The growth curves do not include the tumors that regressed—as shown in Table 4, the tumors shrank/disappeared in 50% of the mice treated with the highest dose of PG-TXL and of the 4 animals with progressively growing tumors at the end of the study, only one had micrometastases in the lungs. So the treatment that reduced growth of the primary tumors also reduced the incidence of metastasis. The incidence of metastasis in all other therapy groups, including the control groups of Cremophor and PG were lower than the PBS control, therefore it is probably not valid to state that the reduction in incidence of metastasis in the Taxol™/Cremophor group is a significant finding.

EXAMPLE 2

DTPA-Paclitaxel

Synthesis of DTPA-Paclitaxel:

To a solution of pacitaxel (100 mg, 0.117 mmol) in dry DMF (2.2 ml) was added diethylenetriaminepentaacetic acid anhydride (DTPA A) (210 mg, 0.585 mmol) at 0° C. The reaction mixture was stirred at 4° C. overnight. The suspension was filtered (0.2 μm Millipore filter) to remove unreacted DTPA anhydride. The filtrate was-poured into distilled water, stirred at 4° C. for 20 min, and the precipitate collected. The crude product was purified by preparative TLC over $C_{18}$ silica gel plates and developed in acetonitrile/water (1:1). Paclitaxel had an $R_f$ value of 0.34. The band above the paclitaxel with an $R_f$ value of 0.65 to 0.75 was removed by scraping and eluted with an acetonitrile/water (1:1) mixture, and the solvent was removed to give 15 mg of DTPA-paclitaxel as product (yield 10.4%): mp:>226° C. dec. The UV spectrum (sodium salt in water) showed maximal absorption at 228 nm which is also characteristic for paclitaxel. Mass spectrum: (FAB) m/e 1229 (M±H)$^+$, 1251 (M±Na), 1267 (M+K). In the $^1$H NMR spectrum (DMSO-d6) the resonance of $NCH_2CH_2N$ and $CH_2COOH$ of DTPA appeared as a complex series of signals at δ2.71–2.96 ppm, and as a multiplet at δ3.42 ppm, respectively. The resonance of C7-H at 4.10 ppm in paclitaxel shifted to 5.51 ppm, suggesting esterification at the 7-position. The rest of the spectrum was consistent with the structure of paclitaxel.

The sodium salt of DTPA-paclitaxel was also obtained by adding a solution of DTPA-paclitaxel in ethanol into an equivalent amount of 0.05 M NaHCO3, followed by lyophilizing to yield a water-soluble solid powder (solubility>20 mg equivalent paclitaxel/ml).

Hydrolytic Stability of DTPA-Paclitaxel:

The hydrolytic stability of DTPA-paclitaxel was studied under accelerated conditions. Briefly, 1 mg of DTPA-paclitaxel was dissolved in 1 ml 0.5 M NaHCO3 aqueous solution (pH 9.3) and analyzed by HPLC. The HPLC system consisted of a Waters 150×3.9 (i.d.) mm Nova-Pak column filled with C18 4 μm silica gel, a Perkin-Elmer isocratic LC pump, a PE Nelson 900 series interface, a Spectra-Physics UV/Vis detector and a data station. The eluant (acetonitrile/methanol/0.02M ammonium acetate=4:1:5) was run at 1.0 ml/min with UV detection at 228 nm. The retention times of DTPA-paclitaxel and paclitaxel were 1.38 and 8.83 min, respectively. Peak areas were quantitated and compared with standard curves to determine the DTPA-paclitaxel and paclitaxel concentrations. The estimated half-life of DTPA-paclitaxel in 0.5 M NaHCO3 solution is about 16 days at room temperature.

Effects of DTPA-Paclitaxel on the Growth of B16 Mouse Melanoma Cells In vitro

Cells were seeded in 24-well plates at a concentration of 2.5×10$^4$ cells/ml and grown in a 50:50 Dulbecco's modified minimal essential medium (OEM) and F12 medium containing 10% bovine calf serum at 37° C. for 24 h in a 97% humidified atmosphere of 5.5% CO2. The medium was then replaced with fresh medium containing paclitaxel or DTPA-paclitaxel in concentration ranging from $5 \times 10^{-9}$ M to $75 \times 10^{-9}$ M. After 40 h, the cells were released by trypsinization and counted in a Coulter counter. The final concentrations of DMSO (used to dissolve paclitaxel) and 0.05 M sodium bicarbonate solution (used to dissolve DTPA-paclitaxel) in the cell medium were less than 0.01%. This amount of solvent did not have any effect on cell growth as determined by control studies.

Figure 2:
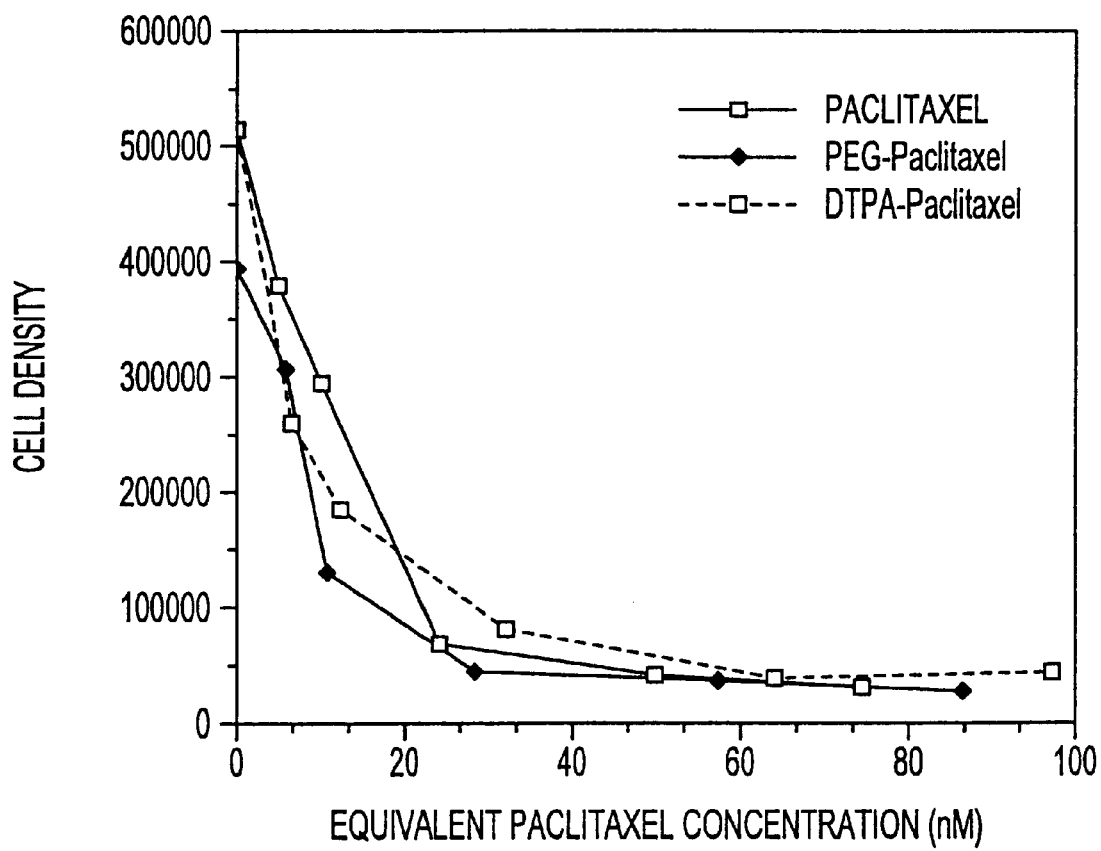
FIG. 2. Effect of paclitaxel, PEG-paclitaxel and DTPA-paclitaxel on proliferation of B16 melanoma cells.

The effects of DTPA-paclitaxel on the growth of B16 melanoma cells are presented in FIG. 2. After a 40-h incubation with various concentrations, DTPA-paclitaxel and paclitaxel were compared as to cytotoxicity. The $IC_{50}$ for paclitaxel and DTPA-paclitaxel are 15 nM and 7.5 nM, respectively.

Antitumor Effect on Mammary Carcinoma (MCa-4) Tumor Model:

Female C3Hf/Kam mice were inoculated with mammary carcinoma (MCa-4) in the muscles of the right thigh ($5 \times 10^5$ cells/mouse). When the tumors had grown to 8 mm (approx. 2 wks), a single dose of paclitaxel or DTPA-paclitaxel was given at 10, 20 and 40 mg equivalent paclitaxel/kg body weight. In control studies, saline and absolute alcohol/ Cremophor 50/50 diluted with saline (1:4) were used. Tumor growth was determined daily, by measuring three orthogonal tumor diameters. When the tumor size reached 12 mm in diameter, the tumor growth delay was calculated. The mice were sacrificed when tumors were approximately 15 mm.

Figure 3:
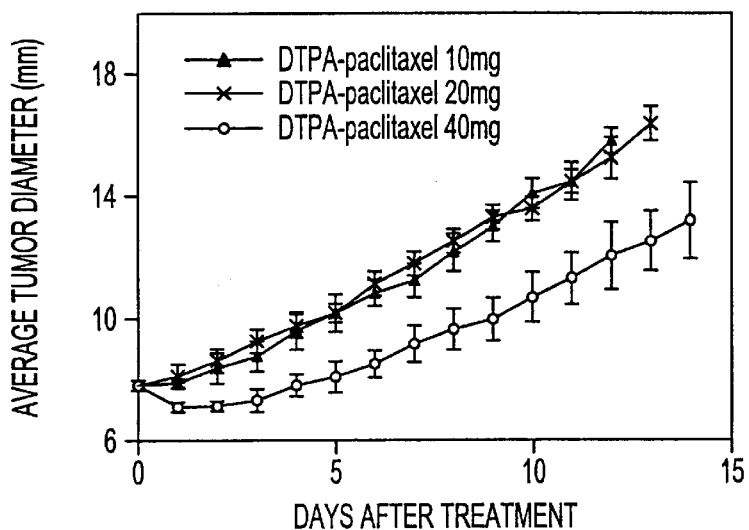
FIG. 3. Antitumor effect of DTPA-paclitaxel on MCa-4 mammary tumors.
Figure 4:
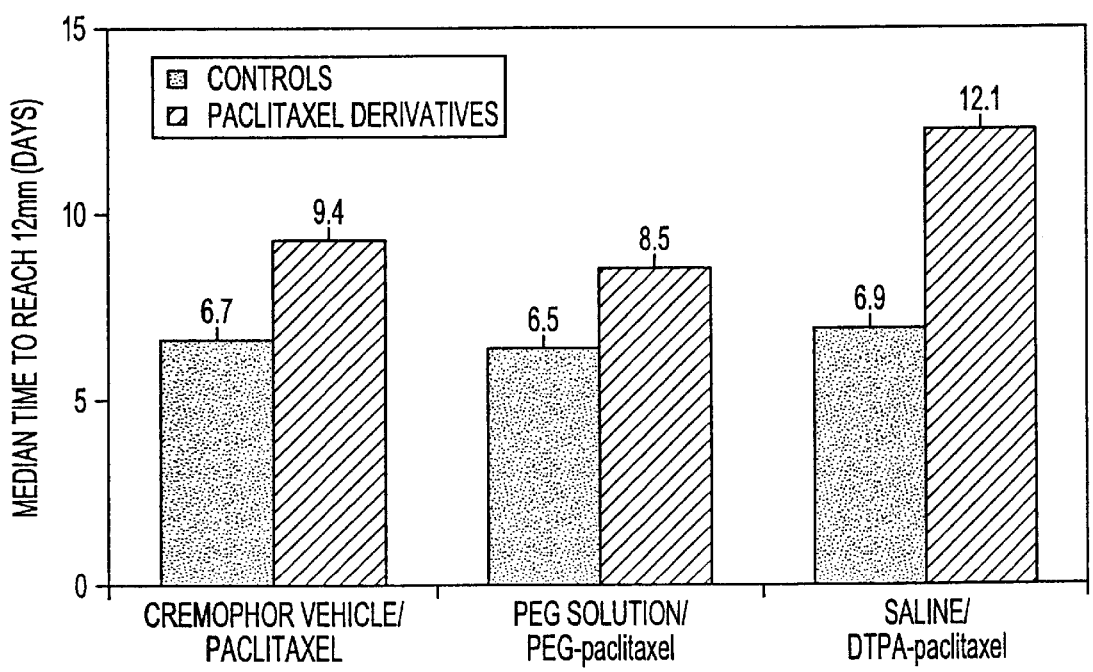
FIG. 4. Median time (days) to reach tumor diameter of 12 mm after treatment with paclitaxel, DTPA-paclitaxel and PEG-paclitaxel.

The tumor growth curve is shown in FIG. 3. Compared to controls, both paclitaxel and DTPA-paclitaxel showed antitumor effect at a dose of 40 mg/kg. The data were also analyzed to determine the mean number of days for the tumor to reach 12 mm in diameter. Statistical analysis showed that DTPA-paclitaxel delayed tumor growth significantly compared to the saline treated control at a dose of 40 mg/kg ($p<0.01$). The mean time for the tumor to reach 12 mm in diameter was 12.1 days for DTPA-paclitaxel compared to 9.4 days for paclitaxel (FIG. 4).

Radiolabeling of DTPA-Paclitaxel with $^{111}$In

Into a 2-ml V-vial were added successively 40 μl 0.6 M sodium acetate (pH 5.3) buffer, 40 μl 0.06 M sodium citrate buffer (pH 5.5), 20 μl DTPA-paclitaxel solution in ethanol (2% w/v) and 20 μl $^{111}$InCl$_3$ solution (1.0 mCi) in sodium acetate buffer (pH 5.5). After an incubation period of 30 min at room temperature, the labeled $^{111}$In-DTPA-paclitaxel was purified by passing the mixture through a CI 8 Sep-Pac cartridge using saline and subsequently ethanol as the mobile phase. Free $^{111}$In-DTPA (<3%) was removed by saline, while $^{111}$In-DTPA-paclitaxel was collected in the ethanol wash. The ethanol was evaporated under nitrogen gas and the labeled product was reconstituted in saline. Radiochemical yield: 84%.

Analysis of $^{111}$In-DTPA-Paclitaxel:

HPLC was used to analyze the reaction mixture and purity of $^{111}$In-DTPA-paclitaxel. The system consisted of a LDC binary pump, a 100×8.0 mm (i.d.) Waters column filled with ODS 5 μm silica gel. The column was eluted at a flow rate of 1 ml/min with a gradient mixture of water and methanol (gradient from 0% to 85% methanol over 15 mm). The gradient system was monitored with a NaT crystal detector and a Spectra-Physics UVIVis detector. As evidenced by HPLC analysis, purification by Sep-Pak cartridge removed most of the $^{111}$In-DTPA, which had a retention time of 2.7 min. The $^{111}$In-DTPA was probably derived from traces of DTPA contaminant in the DTPA-paclitaxel. A radiochromatogram of $^{111}$In-DTPA-paclitaxel correlated with its UV chromatogram, indicating that the peak at 12.3 min was indeed the target compound. Under the same chromatographic conditions, paclitaxel had a retention time of 17.1 min. The radiochemical purity of the final preparation was 90% as determined by HPLC analysis.

Figure 5:
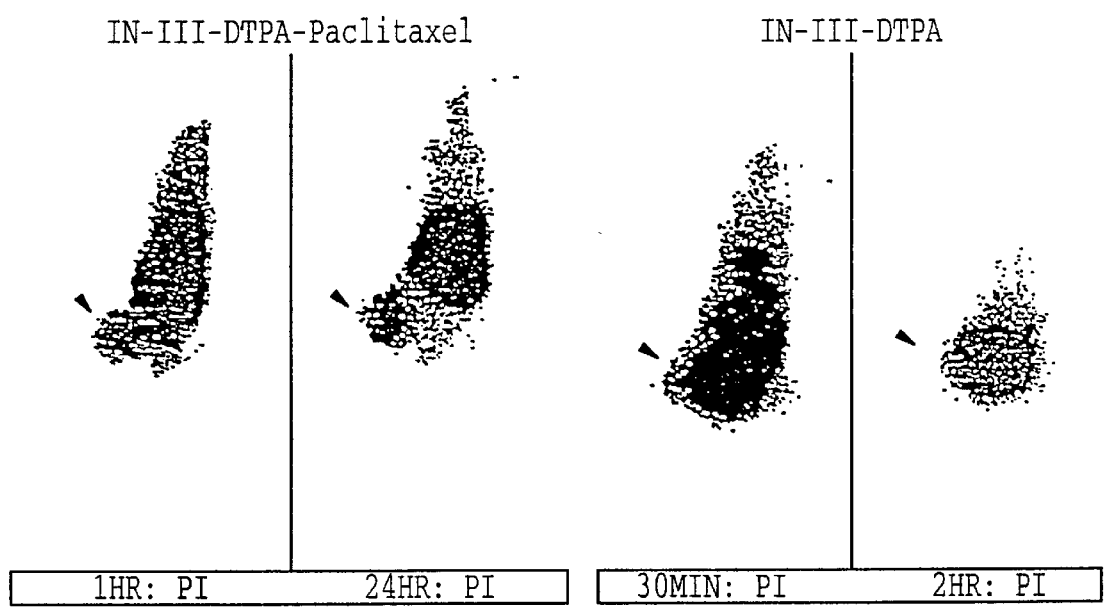
FIG. 5. Gamma-scintigraphs of mice bearing MCa-4 tumors following intravenous injection of $^{111}$In-DTPA-paclitaxel and $^{111}$In-DTPA. Arrow indicates the tumor.

Whole-Body Scintigraphy:

Female C3Hf/Kam mice were inoculated with mammary carcinoma (MCa-4) in the muscles of the right thigh ($5 \times 10^5$ cells). When the tumors had grown to 12 mm in diameter, the mice were divided into two groups. In group 1, the mice were anesthetized by intraperitoneal injection of sodium pentobarbital, followed by $^{111}$In-DTPA-paclitaxel (100–200 mCi) via tail vein. A γ-camera equipped with a medium energy collimator was positioned over the mice (3 per group). A series of 5 min acquisitions were collected at 5, 30, 60, 120, 240 min and 24 h after injection. In group 11, the same procedures were followed except that the mice were injected with $^{111}$In-DTPA as a control. FIG. 5 shows gamma-scintigraphs of animals injected with $^{111}$In-DTPA and $^{111}$In-DTPA-paclitaxel. $^{111}$In-DTPA was characterized by rapid clearance from the plasma, rapid and high excretion in the urine with minimal retention in the kidney and negligible retention in the tumor, the liver, the intestine and other organs or body parts. In contrast, $^{111}$In-DTPA-paclitaxel exhibited a pharmacological profile resembling that of paclitaxel (Eiseman et al., 1994). Radioactivity in the brain was negligible. Liver and kidney had the greatest tissue:plasma ratios. Hepatobmliary excretion of radiolabeled DTPA-paclitaxel or its metabolites was one of the major routes for the clearance of the drug from the blood. Unlike paclitaxel, a significant amount of "In-DTPA-paclitaxel was also excreted through kidney, which only played a minor role in the clearance of paclitaxel. The tumor had significant uptake of $^{111}$In-DTPA-paclitaxel. These results demonstrate that $^{111}$In-DTPA-paclitaxel is able to detect certain tumors and to quantify the uptake of $^{111}$In-DTPA-paclitaxel in the tumors, which in turn, may assist in the selection of patients for the paciitaxel treatment. In contrast, the smaller PG-TXL conjugate has a different distribution than DTPA-paclitaxel, and partly localizes in the liver and tumors of test animals.

EXAMPLE 3

Polyethylene Glycol-Paclitaxel

Synthesis of Polyethylene Glycol-Paclitaxel (PEG-Paclitaxel)

The synthesis was accomplished in two steps. First 2'-succinyl-paclitaxel was prepared according to a reported procedure (Deutsch et al., 1989). Paclitaxel (200 mg, 0.23 mmol) and succinic anhydride (288 mg, 2.22 mmol) were allowed to react in anhydrous pyridine (6 ml) at room temperature for 3 h. The pyridine was then evaporated, and the residue was treated with water, stirred for 20 mm, and filtered. The precipitate was dissolved in acetone, water was slowly added, and the fine crystals were collected to yield 180 mg 2'-succinyl-paclitaxel. PEG-paciitaxel was synthesized by an N-ethoxycarbonyl-2-ethoxy-1,2-dihydroquinoline (EEDQ) mediated coupling reaction. To a solution of 2'-succinyl-paclitaxel (160 mg, 0.18 mmol) and methoxypolyoxyethylene amine (PEG-NH$_2$, MW 5000, 900 mg, 0.18 mmol) in methylene chloride was added EEDQ (180 mg, 0.72 mmol). The reaction mixture was stirred at room temperature for 4 h. The crude product was chromatographed on silica gel with ethyl acetate followed by chloroform-methanol (10:1). This gave 350 mg of product. $^1$H NMR (CDCl$_3$) δ 2.76 (m, succinic acid, COCH$_2$CH$_2$CO), δ 3.63 (PEG, OCH$_2$CH$_2$O), δ 4.42 (C7-

H) and δ 5.51 (C2'-H). Maximal UV absorption was at 288 nm which is also characteristic for paclitaxel. Attachment to PEG greatly improved the aqueous solubility of paclitaxel (>20 mg equivalent paclitaxel/ml water).

Hydrolytic Stability of PEG-Paclitaxel

PEG-Paclitaxel was dissolved in phosphate buffer (0.01M) at various pHs at a concentration of 0.4 mM and the solutions were allowed to incubate at 37° C. with gentle shaking. At selected time intervals, aliquots (200 μl) were removed and lyophilized. The resulting dry powders were redissolved in methylene chloride for gel permeation chromatography (GPC analysis). The GPC system consisted of a Perkin-Elmer PL gel mixed bed column, a Perkin-Elmer isocratic LC pump, a PE Nelson 900 series interface, a Spectra-Physics UV/Vis detector and a data station. The elutant (methylene chloride) was run at 1.0 ml/min with the UV detector set at 228 nm. The retention times of PEG-paclitaxel and paclitaxel were 6.1 and 8.2 min, respectively. Peak areas were quantified and the percentage of PEG-paclitaxel remaining and the percentage of paclitaxel released were calculated. The half life of PEG-paclitaxel determined by linear least-squares at pH 7.4 was 54 min. The half-life at pH 9.0 was 7.6 min. Release profiles of paclitaxel from PEG-paclitaxel at pH 7.4 is shown in FIG. 8.

Cytotoxicity Studies of PEG-Paclitaxel Using B16 Mouse Melanoma Cells In Vitro

Following the procedure described in the cytotoxicity studies with DTPA-paclitaxel melanoma cells were seeded in 24-well plates at a concentration of $2.5 \times 10^4$ cells/ml and grown in a 50:50 Dulbecco's modified minimal essential medium (DME) and F12 medium containing 10% bovine calf serum at 37° C. for 24 h in a 97% humidified atmosphere of 5.5% $CO_2$. The medium was then replaced with fresh medium containing paclitaxel or its derivatives in concentrations ranging from $5 \times 10^{-9}$ M to $75 \times 10^{-9}$ M. After 40 h, the cells were released by trypsinization and counted in a Coulter counter. The final concentrations of DMSO (used to dissolve paclitaxel) and 0.05 M sodium bicarbonate solution (used to dissolve PEG-paclitaxel) in the cell medium were less than 0.01%. This amount of solvent did not have any effect on cell growth as determined by control studies. Furthermore, PEG in the concentration range used to generate an equivalent paclitaxel concentration from $5 \times 10^{-9}$ M to $75 \times^{-9}$ M also did not effect cell proliferation.

Antitumor Effect of PEG-Paclitaxel Against MCa-4 Tumor in Mice

To evaluate the antitumor efficacy of PEG-paclitaxel against solid breast tumors, MCa-4 cells ($5 \times 10^5$ cells) were injected into the right thigh muscle of female C3Hf/Kam mice. As described in Example 1 with the DTPA-paclitaxel, when the tumors were grown to 8 mm (Approx. 2 wks), a single dose of paclitaxel or PEG-paclitaxel was given at 10, 20 and at 40 mg equivalent paclitaxel/kg body weight. Paclitaxel was initially dissolved in absolute ethanol with an equal volume of Cremophor. This stock solution was further diluted (1:4 by volume) with a sterile physiological solution within 15 min of injection. PEG-paclitaxel was dissolved in saline (6 mg equiv. paclitaxel/ml) and filtered through a sterile filter (Millipore, 4.5 μm). Saline, paclitaxel vehicle, absolute alcohol:Cremophor (1:1) diluted with saline (1:4) and PEG solution in saline (600 mg/kg body weight) were used in control studies. Tumor growth was determined daily, by measuring three orthogonal tumor diameters. When the tumor size reached 12 mm in diameter, the tumor growth delay was calculated.

The tumor growth curve is shown in FIG. 9. At a dose of 40 mg/kg, both PEG-paclitaxel and paclitaxel effectively delayed tumor growth. Paclitaxel was more effective than PEG-paclitaxel, although the difference was not statistically significant. Paclitaxel treated tumors required 9.4 days to reach 12 mm in diameter whereas PEG-paclitaxel-treated tumors required 8.5 days. Statistically, these values were significant (p>0.05) as compared to their corresponding controls, which were 6.7 days for the paclitaxel vehicle and 6.5 days for the saline solution of PEG (FIG. 4).

EXAMPLE 5

Poly(L-glutamic acid)-Paclitaxel (PG-TXL) and Paclitaxel Pharmacological Properties The objective of this study was to compare PG-TXL and paclitaxel pharmacological properties in their ability to promote in vitro assembly of tubulin, to inhibit cell growth against rat mammary tumor cell line 13762F and human breast tumor cell lines, to induce p53 protein, and to rescue a paclitaxel-dependent mutant cell line. Paclitaxel's release from PG-TXL in vivo was measured to determine if PG-TXL's mechanism of action can be attributed to free pacitaxel.

Microtubule Polymerization Using Poly-Glutamic Acid-Paclitaxel (PG-TXL) and Paclitaxel To test whether intact PG-TXL has any intrinsic biological activity in promoting tubulin polymerization, paclitaxel, PG-TXL, and "aged" PG-TXL were compared for their relative ability to promote in vitro assembly of purified bovine brain tubulin. The tubulin assembly reaction was performed at 32° C. in PEM buffer (80 mM PIPES buffer, 1 mM EGTA, 1 mM $MgCl_2$, pH 6.9) at a tubulin (bovine brain, Cytoskeleton Inc., Boulder, Colo.) concentration of 1 mg/ml (10 μM) in the presence or absence of drugs (1.0 μM equivalent paclitaxel) and 1.0 mM guanosine 5'-triphosphate (GTP). "Aged" PG-TXL was obtained by placing PG-TXL in PBS (pH 7.4) at 37° C. for 3 days. Tubulin polymerization was followed by measuring the absorbance of the solution at 340 nm over time. Addition of 1 μM paclitaxel to a solution of tubulin in assembly buffer caused a clear increase in absorbance due to the increase in light scattering resulting from the polymerization of tubulin into microtubules. In contrast, a 10 μM paclitaxel equivalent of PG-TXL had no effect on polymerization. A solution of the conjugate that was "aged" for 3 days in PBS (pH 7.4) at 37° C. exhibited enhanced activity although its ability to promote tubulin polymerization was still markedly less than paclitaxel (FIG. 10).

Effects of Poly-Glutamic Acid-Paclitaxel (PG-TXL) on the Growth of Rat and Human Tumor Cell Lines In Vitro To evaluate whether the superior antitumor activity of PG-TXL observed in animals is due to increased cytotoxicity, PG-TXL and paclitaxel were compared for their ability to inhibit cell growth against the established rat mammary tumor cell line 13762F. The effect of PG-TXL on cell growth was examined by a plating efficiency assay. Rat 13762F cells were seeded (200 cells) into 60 mm dishes containing drug concentrations varying from 0 to 200 nM in growth medium (α modified minimum essential medium [α-MEM] containing 5% fetal bovine serum, 50 U/ml of penicillin, and 50 μg/ml of streptomycin). After 6 days of growth, the cells were stained with a 0.1% methylene blue solution and colonies were counted. The drug concentration producing 50% inhibition of colony formation ($IC_{50}$) was then calculated. The approximate $IC_{50}$ values after 6 days of continuous exposure were: paclitaxel (2 nM), PG-TXL (100 nM), "aged" (see below) PG-TXL (50 nM). It is clear that PG-TXL is approximately 30–50 fold less potent than paclitaxel itself. When PG-TXL was incubated in phosphate buffered saline solution (PBS, pH 74) at 37° C. for 3 days to obtain an "aged" solution, only about 10% of paclitaxel was released. Since the "aged" solution is more potent than freshly dissolved PG-TXL, the in vitro degradation of PG-TXL or release of active drug appears to be important for PG-TXL to exert this biological activity. However, even after "aging," PG-TXL is still 25 times less potent than paclitaxel.

In a similar study, the effect of PG-TXL on cell growth of human breast cancer cell lines was examined by MTT assay after 3 days of continuous exposure. While PG-TXL was 8-and 30-fold more potent than paclitaxel against MDA330 and MDA-MB453 cell lines, PG-TXL was 2- and 3-fold less potent than paclitaxel against MCF7/her-2 and MCF7 cell lines. These results suggest that PG-TXL and paclitaxel have different activity against different cell lines. PG-TXL may be a product with distinct pharmacological properties different from that of paclitaxel.

The Ability of Poly-Glutamic Acid-Paclitaxel (PG-TXL) to Support a Paclitaxel-Dependent Cell Line In Vitro The inventors investigated the ability of PG-TXL to rescue a paclitaxel-dependent mutant cell line. Tax 18, a CHO cell line selected for resistance to paclitaxel, is a well characterized mutant that has been found to require the continuous presence of paclitaxel for cell division. In the absence of drug, a functional mitotic spindle apparatus is unable to form (Cabral et al. 1983). The mitosis phase of the cell cycle is prolonged with subsequent failure to segregate chromosomes and to divide into daughter cells. Nonetheless, the cells continue to progress through the cell cycle and replicate their DNA resulting in the formation of large polyploid cells that eventually die due to genomic instability (Cabras and Barlow, 1991). Low concentrations of paclitaxel are able to rescue the mutant phenotype by permitting microtubule assembly and the formation of sufficient mitotic spindle fibers. Thus, these cells provide a convenient bioassay-for agents that promote microtubule assembly. Growth of paclitaxel-dependent CHO mutant Tax-18 cells was carried out on 24-well tissue culture dishes. Approximately 100 cells were added to wells containing growth medium and equivalent concentrations of paclitaxel varying from 0 to 1.0 $\mu$M. After 6 days of incubation at 37° C., the medium was removed and the cells were stained with methylene blue.

Little or no increase in cell number is seen in the absence of drug, but concentrations of paclitaxel between 0.05–0.2 $\mu$M clearly support the growth of this cell line. Higher concentrations of paclitaxel are presumably toxic to the cells because of overstabilization of the microtubules as is observed for normal cells. On the other hand, freshly prepared PG-TXL shows little ability to rescue Tax-18 cell growth even at the highest paclitaxel-equivalent concentration tested (1 $\mu$M). When PG-TXL was "aged" by incubating in PBS for 6 days at 37° C., its ability to support Tax-18 cell growth was partially restored. These data indicate that PG-TXL does not promote microtubule assembly, and that the in vitro biological activity of "aged" PG-TXL is a contribution of paclitaxel released from poly-glutamic acid-paclitaxel (PG-TXL).

The Release of [$^3$H]paclitaxel from PG-[$^3$H]TXL In Vivo

To assess the pharmacokinetic and release characteristics of paclitaxel in vivo, normal female C3Hf/Kam mice (25–30 g) were injected with a dose of 20 mg equivalent [$^3$H] paclitaxel or PG-[$^3$H]paclitaxel intravenously into the tail vein. Each mouse received 6 $\mu$Ci of radiolabeled drug. [$^3$H]paclitaxel was dissolved in Cremophor EL® vehicle whereas PG-[$^3$H]paclitaxel was dissolved in saline. Volume injected into each mice was between 0.2 to 0.3 ml. At 0, 5, 15, 30 min, and 1, 2, 4, 8, 16, 24, 48 h postinjection, animals were sacrificed and blood samples were collected (4–5 mice per time point). Total radioactivity in plasma was measured by liquid scintillation counting (Beckman Model LS 6500, Fullerton, Calif.) using 10 $\mu$l aliquots of plasma. Up to 200 $\mu$l plasma was extracted with 3 volume of ethyl acetate according to Longnecker et al. (1987). The extraction efficiency for paclitaxel was 80%. The samples were centrifuged for 5 min at 2500 rpm, and the supernatant was separated and brought to dryness. The dried extract was reconstituted with 195 $\mu$l of HPLC mobile phase, mixed with 5 $\mu$l of cold paclitaxel (0.2 mg/ml), and 100 $\mu$l was injected onto the HPLC for determination of free paclitaxel radioactivity. Pharmacokinetic parameters were analyzed by a noncompartmental model using the WinNonlin software package. Each data point generated was the mean value of 4–5 mice.

The clearance of both drugs from plasma is shown in FIG. 11. While paclitaxel has an extremely short half life in plasma of mice ($t_{1/2}$, 29 min), the apparent half life of PG-TXL is prolonged ($t_{1/2}$, 317 min). Slower clearance of PG-TXL from the blood was a design feature of the polymer-drug conjugate with the goal of improving tumor uptake. Surprisingly, the rate of conversion of PG-TXL to paclitaxel in plasma is slow with less than 0.1% of the radioactivity from PG-[$^3$H]TXL being recovered as [$^3$H] paclitaxel within 144 h after drug injection (FIG. 11).

In a separate study, mice bearing OCA-1 tumors were prepared as described previously. When the tumor reached 500 mm$^3$, animals were injected with a dose of 20 mg equivalent paclitaxel/kg of [$^3$H]paclitaxel or PG-[$^3$H]TXL into the tail vein. Animals were killed at 2, 5, 9, 24, 48, and 144 h postinjection. Tumors were removed, weighed, and homogenized with 3 volume of PBS (w/v). Percent of injected dose per gram tissue is calculated based on total radioactivity associated with the tumor, which was determined by counting prepared tissue homogenate aliquots. An aliquot of tissue homogenate was mixed with tissue solubilizer, followed by addition of scintillation solvent, and counted for total radioactivity. The counting efficiency was verified by the method of standard addition. Alternatively, aliquots of tissue homogenates were extracted with ethyl acetate and analyzed for free paclitaxel by HPLC. The HPLC system consisted of a 150×3.9 mm Nova-Pak column (Waters, Milford, Mass.), a liquid chromatography pump (Waters model 510), a UV/Vis detector set at 228 nm (Waters model 486), a flow scintillation analyzer (Packard model 500TR, Downers Grove, Ill.), and a Packard radiomatic software for data analysis. The eluting solvent (methanol:watter=2:1) was run at 1.0 ml/min. The uptake of total drugs in OCA-1 tumor was expressed as a percentage of the administered dose per gram of tissue and the association of radioactivity within OCA-1 tumor as free paclitaxel was expressed as dpm per gram tissue.

Quantitative assessment of tumor uptake in C3Hf/Kam mice showed that relatively high levels of radioactivity from radiolabeled PG-TXL appear in tumor tissue shortly after injection (FIG. 12A) as compared to radiolabeled paclitaxel. However, only small amounts of radioactivity within tumor tissue are due to the release of free paclitaxel (FIG. 12B). Data are presented in FIG. 12A and FIG. 12B as mean±SD from 3 mice per time point. The percent of radioactivity within tumor tissue due to paclitaxel does not appreciably increase with time suggesting that PG-TXL is not simply a prodrug for the gradual release of paclitaxel.

In contrast to paclitaxel, in vitro studies with PG-TXL whether prepared as a fresh solution or even after "aging" in buffer have clearly shown that the complex is not a potent cytotoxic species. It neither strongly supports tubulin polymerization nor the growth and survival of a paclitaxel-dependent CHO cell line. Furthermore, data obtained from pharmacokinetic studies indicate that both the extent and rate of release of paclitaxel in plasma is very low (less than 0.1% in 144 h). While the uptake of PG-TXL material was some 5-fold greater than that achieved by paclitaxel when using equivalent antitumor doses, that material which gains entry into tissues exists in the tissue mainly in form(s) which have been shown not to be free paclitaxel.

EXAMPLE 6

Effect of Polymer Structure on Activity of Water soluble polyamino Acid-Paclitaxel Conjugates.

The present study evaluated whether antitumor activities of polymer-paclitaxel conjugates were affected by the structure of polyamino acids used for drug conjugation. Paclitaxel was coupled to poly(l-glutamic acid), poly(d-glutamic acid), and poly(laspartic acid) according to previously described procedures. These polyamino acidpaclitaxel conjugates had similar paclitaxel content, aqueous solubility, and molecular weight (30–40K). In C3Hf/Kam mice bearing murine OCA-1 ovarian cancer (500 mm$^3$ at time of treatment), a single i.v. injection of poly(l-glutamic acid)-paclitaxel at 80 mg equiv. paclitaxel/kg body weight produced a tumor growth delay of 21 days vs. saline treated controls. Poly(d-glutamic acid)-paclitaxel was as effective as poly(l-glutamic acid)-paclitaxel. However, paclitaxel conjugated with poly(l-aspartic acid) was completely inactive against OCA-1 tumor. In a separate study, the antitumor activity of polymer-paclitaxel conjugates of different molecular weight (1K, 13K, and 36K) was compared. Conjugates of lower molecular weight were significantly less effective than conjugate of higher molecular weight. The higher molecular weights above 50,000 was too viscous.

EXAMPLE 7

Poly-glutamic Acid-Paclitaxel (PG-TXL) Induces less Apoptosis Compared to Paclitaxel.

To assess the mechanism of PG-TXL associated antitumor activity, histological sections of OCA-1 tumors excised from paclitaxel and PG-TXL treated mice were examined. OCA-1 tumor bearing mice were prepared as previously described. When tumor volume reached 500 mm$^3$, animals were injected with either paclitaxel (80 mg/kg) or PG-TXL (160 mg equivalent paclitaxel/kg). At different times ranging from 0 to 144 h after treatment, tumors were histologically analyzed to quantify mitotic and apoptotic activity according to Milas et al. (1995). The mice were killed by cervical dislocation and the tumors were immediately excised and placed in neutral-buffered formalin. The tissues were then processed and stained with hematoxylin and eosin. Both mitosis and apoptosis were scored in coded slides by microscopic examination at 400× magnification. Five fields of nonnecrotic areas were randomly selected in each histological specimen, and in each field the number of apoptotic nuclei and cells in mitosis were recorded as numbers per 100 nuclei and were expressed as a percentage. The values were based on scoring 1500 nuclei obtained from 3 mice per time point.

The changes observed in the paclitaxel-treated mice were qualitatively similar to those previously described (Milas et al., 1995). The tumor cells showed marked nuclear fragmentation with formation of apoptotic bodies, which was especially marked on day 1 (FIG. 13). Viable tumor cell clumps with normal mitoses were still present in these tumors by 144 h, indicating that these tumors would eventually regrow. Treatment with PG-TXL only resulted in a mild increase in mitotically arrested cells and apoptotic cells, presumably due to the small amount of free paclitaxel released from PG-TXL (FIG. 13). By 96 h, tumors from PG-TXL-treated mice developed extensive edema and necrosis, and only a small rim of viable tumor cells remained. By 144 h, the residual tumor clumps as compared to controls were comprised of cells that were larger, more pleomorphic, and that displayed less mitotic activity.

These data suggest that the water-soluble PG-TXL conjugate of the present disclosure has superior antitumor efficacy with reduced toxicity as compared to conventional free paclitaxel preparations. Although originally designed as a water-soluble form of paclitaxel, it is now clear that the agent used to solubilize paclitaxel, contributes to the overall anti-tumor activity of this remarkable new complex. These data indicate that PG-TXL has an ability to produce cell death in a manner which is separate from and in addition to the apoptosis produced by released free paclitaxel.

EXAMPLE 8

Synthesis of Poly-Glutamic Acid-Camptothecin (PG-CPT) Conjugate.

The synthesis of PG-CPT followed a similar reaction as previously described for the synthesis of PG-TXL. Into 80 mg of PG polymer in 2.5 ml dry DMF was added 20 mg CPT (Hande Tech.), 34 mg DCC, and trace amount of DMAP as catalyst. After stirred at room temperature overnight, the reaction mixture was poured into chloroform, and the precipitate collected. The dried precipitate was redissolved in sodium carbonate solution, dialyzed against 0.05 M phosphate buffer (pH4.5), filtered, and lyophilized. The content of CPT in the polymer conjugate was determined by fluorescence spectrometer (Perkin-Elmer Model MPF-44A) using emission wavelength of 430 nm and excitation wavelength of 370 nm. Content: 2% to 5% (w/w), solubility: >200 mg conjugate/ml.

EXAMPLE 9

Synthesis of Poly-Lysine (PL) TXL Conjugate (PL-TXL).

All accessible amine functional groups of poly-lysine (MW>30,000, Sigma) will be converted to carboxylic acid functional groups by reacting poly-lysine with succinic anhydride, glutaric anhydride, or DTPA. The remaining unreacted NH2 group in polylysine will be blocked by reacting the modified polymer with acetic anhydride. TXL, docetaxel, other taxiods, etopside, teniposide, camptothecin, epothilone or other anti-tumor drugs will be conjugated to the resulting polymer according to previously described procedures for the synthesis of PG-TXL.

EXAMPLE 10

Synthesis of Other Polyamino Acids to be Used to Conjugate TXL.

Polyamino acid copolymers containing glutamic acid may be synthesized by the copolymerization of N-carboxyanhydrides (NCAs) of corresponding amino acid with gamma-benzyl-L-glutamate NCA. The resulting benzyl glutamate-containing copolymer will be converted to glutamic acid-containing copolymer by removing the benzyl protecting group (FIG. 15). TXL, docetaxel, other taxiods, etopside, teniposide, camptothecin, epothilone or other antitumor drugs will be conjugated to the resulting polymer according to previously described procedures for the synthesis of PG-TXL and PG-CPT.

EXAMPLE 11

Use of PG-TXL in Humans

Introduction

Poly-L-glutamic acid-Paclitaxel (PG-TXL) is a conjugate of poly-L-glutamic acid and paclitaxel. This compound is water soluble and based on early animal studies it appears that it can be administered as a short, that is several minute, intravenous injection. Based on the in vitro and early animal work, it appears that this compound is at least as active against cancer as the monomeric paclitaxel in Cremophor and may have fewer side effects. Based on these observations, this drug will be studied in humans. The study will first require formulation of this compound in a solvent which is commonly used for intravenous infusion. The inventors expect that either normal saline, 5% dextrose in water or sterile water will be used as the solvent. This formulation of PG-TXL will then be administered to at least two species of test animals such as rats and dogs to determine the toxicities of the drug in those animals and to determine a dose of the drug which then can serve as the lowest starting dose for a Phase I human study. That Phase I human study will define a dose of PG-TXL which may be used in subsequent Phase II studies in patients. Phase II studies will be performed in several tumor types to determine the activity of PG-TXL in various cancers. One of ordinary skill in the art will recognize that modifications in administration, selection of animal models and dose regiments may be made in the methods disclosed in following example, and such modifications are encompassed by the invention.

Animal Studies

These studies will be performed in rats and Beagle dogs with approximately 3 animals studied at each dose level of the drug. The levels will be increased until life threatening toxicity is noted. The animals will undergo blood testing as well as necropsy to determine the organ systems which are susceptible to this drug's toxicity and therefore to expect the side effects in human studies. Once the dose is determined which causes the death of 10% of animals then the equivalent of one-tenth of that dose will be recommended as the starting dose for human studies. This is the usual recommendation by the Food and Drug Administration (FDA) as the initial dose for human Phase I studies.

Phase I Studies

Phase I study of this drug will be performed using the starting dose defined in animal studies. The drug will be injected into the vein by a syringe over several mm or alternatively it may be infused as a short infusion, up to approximately 10 to 15 min. The volume of the solvent will be from 10 ml to approximately 100 ml depending on which of the two intravenous injection approaches are used. The drug will be administered every 3 wk. This schedule is based on the early animal studies and on the schema used with paclitaxel in Cremophor. Three patients will be started on the lowest dose level as defined by the animal studies and will be treated with an injection of PG-TXL. Blood tests will be performed at baseline and weekly to evaluate blood counts; tests of liver function and renal function will be performed every 3 wk. It is expected that the counts and physiological parameters will recover sufficiently from the PG-TXL to resume the next cycle of treatment 3 wk after the previous one. If this is the case then the treatment will be repeated every 3 wk. If the first cohort of three patients tolerates the drug for 3 wk then these patients will be allowed to have the dose increased by a predetermined schema that is usually used in the Phase I studies. Once three patients have tolerated the first cycle, the next cohort of 3 patients will be started on the next higher dose level. This process of increasing the dose level will continue until at least 2 out of 3 patients at a dose level have side effects which are so severe that they prohibit continuing administration of the drug. In such a circumstance the dose level just prior to the excessively toxic one will be considered the level of drug to be administered in subsequent studies. Six to ten patients shall be treated on the dose level which will be recommended for Phase II studies to confirm its tolerability. Once the appropriate dose has been defined and acute toxic side effects of the drug evaluated, Phase II studies will be initiated.

Phase II Studies

Phase II studies of PG-TXL will be performed in several tumor types. Each study will be designed in a usual standard Phase II manner following either Gahan's or Simon's design. In brief, approximately 14 patients of a given tumor type will be treated initially, if there is no evidence of anti-cancer activity in that tumor type then further studies of PG-TXL in that tumor type will be aborted. However, if at least one patient has clinical benefit, defined as at least 50% decrease in the sum of products of perpendicular cross-sectional diameters of the tumors, then the number of patients with that tumor type treated with PG-TXL will be increased to 30. These studies will allow us to define the activity of PG-TXL in various cancers and refine the information on the side effects of the drug. The tumor types of special interest for PG-TXL will be the ones which have shown good response to paclitaxel and docetaxel. This will include ovarian cancer, breast cancer, and lung cancer. Studies comparing poly-glutamic acid-paclitaxel to paclitaxel in tumors showing response to PG-TXL will be performed. Such studies are called Phase III studies.

Phase III Studies of PG Paclitaxel

Based on the activity of paclitaxel in ovarian cancer, breast cancer, and lung cancer these will be the tumor types in which PG-TXL will be compared to paclitaxel. In view of the necessity to have a large number of patients in such randomized studies, the inventors expect that a multi-institutional study will be necessary. The inventors have in their institution access to Cooperative Community Oncology Program (CDDP) and to many other multi-institutional study groups. In addition to the potential clinical benefit of PG-TXL vs. paclitaxel, it would be appropriate to evaluate the economic impact of the two drugs. It is expected that a short term infusion of PG-TXL may result in a less costly treatment. And, therefore, there is an expectation that PG-TXL may be cost effective relative to paclitaxel monotherapy. Not only is the infusion going to be shorter, it is expected that in view of the absence of Cremophor fewer side effects will be experienced by the patients and therefore the premedication regiment including steroids and intravenous H2 and Hi blockers may no longer be necessary. All of these factors will result in a reduction in the cost of the treatment.

Summary

It is expected that the initial animal toxicology evaluation will require up to 6 months. Subsequent to that, if a drug formulation is available, human Phase I studies may be completed in another 6 to 9 months. Once these have been completed, Phase II studies in various tumor types may take another 6 to 9 months. At that point, the inventors will have a good idea of the efficacy of this drug and targeted Phase III studies may be designed and initiated. It is also possible that the Phase II studies will show enough clinical activity that abbreviated Phase III studies or no Phase IU studies would be necessary.

EXAMPLE 12

Enhancement of Tumor Radioresponse of a Murine Ovarian Carcinoma by Poly(L-Glutamic Acid)-Paclitaxel Conjugate Introduction The combination of chemotherapy and radiation therapy in the treatment of a variety of tumors has produced substantial improvement in complete response and survival rates (Rotman, 1992). Both in vitro and in vivo studies have demonstrated that paclitaxel can strongly enhance tumor radioresponse. In animal studies, the enhancement factors range from 1.2 to more than 2.0, depending on the tumor type, drug concentration, and dose scheduling. This study investigated the radiosensitization effects of poly(L-glutamic acid)-paclitaxel (PG-TXL).

Experimental Methods

PG-TXL was synthesized as described herein from poly (L-glutamic acid) (Sigma, viscosity molecular weight: 31 K). The conjugate contained 20% paclitaxel (w/w) which was coupled to PG via ester linkages. Female C3HL'Kam mice were inoculated i.m. in the right hind leg with $5 \times 10^5$ ovarian OCa-1 carcinoma cells. When tumors reached 8 mm in diameter, mice were randomly divided into 12 groups with each group consisting of 6–12 mice. Mice in groups—1–5 were given saline, 14 Gy irradiation alone, or PG-TXL alone at doses of 47, 80 or 120 mg eg. paclitaxel/kg. Mice in groups 6–9 were given PG-TXL at 47 mg eg. Paclitaxel/kg and 14 Gy local irradiation at 2, 24, 48, and 144 h after PG-TXL treatments. Group 10 was given PG-TXL at 80 mg eg paclitaxel/kg and 14 Gy at 24 h after PG-TXL treatment. Groups 11 and 12 was given PG-TXL at 120 mg eq. Paclitaxel/kg and 14 Gy at 24 h prior or 24 h after PG-TXL treatment. PG-TXL was given in a single intravenous injection. Local gamma irradiation to the tumor was delivered from a $^{137}Cs$ irradiator at a dose rate of 7 Gy per minute. Tumor growth delay was determined by measuring three orthogonal tumor diameters until tumors reached 14 mm in diameter.

Results and Discussion

The radiosensitization effects of PG-TXL were dose dependent.

At the lower PG-TXL dose of 47 mg eq. Paclitaxel/kg, a subadditive effect was observed. The mean enhancement factors varied from 0.54 to 0.75 depending on the timing of radiation delivery. However, a superadditive effect was observed at higher doses of PG-TXL. The mean enhancement factors increased from 0.75 to 1.8 and 4.2 when PG-TXL was given at 24 h prior to irradiation and PG-TXL doses were increased from 47 to 80 and 120 mg eg. Paclitaxel/kg (Table 7). The subadditive effect of chemoradiation observed with PG-TXL at the lower dose may be attributed to inadequate cell killing and rapid repopulation of surviving cells. At higher doses, PG-TXL may have profound effects on population of cycling tumor cells and/or on tumor reoxygenation, resulting in significantly enhanced radiosensitization effect. Interestingly, when tumors were irradiated at 14 Gy prior to treatment with PG-TXL at 120 mg eq. paclitaxel/kg, a superadditive effect with an enhancement factor of 4.3 was observed (Table 7). This result contrasts with previous observation that paclitaxel induces radiation resistance when it was given after irradiation (Ingram and Redpath, 1997).

TABLE 7

Effect of PG-TXL on Radioresponse of Murine Ovarian OCa-1 Tumor

| Treatments | Radiation (14 GY) | Days for tumor to grow from 8–14 mm (means ± SD) | Absolute growth delay in days[a] | Normalized growth delay (means ± SD)[b] | Enhancement factors (95% C.I.)[c] |
|---|---|---|---|---|---|
| Saline | No | 17.2 ± 2.2 | | | |
| PG-TXL 47 mg eq./kg | No | 19.8 ± 0.98 | 2.7 | | |
| PG-TXL 80 mg eq./kg | No | 25.3 ± 3.9 | 8.1 | | |
| PG-TXL 120 mg eq/kg | No | 29.7 ± 3.2 | 12.5 | | |
| 14 Gy radiation alone | Yes | 37.9 ± 6.1 | 20.7 | | |
| PG-TXL 47 mg eq./kg | Yes | 35.3 ± 4.7 | 18.2 | 15.5 ± 4.7 | 0.75 (0.5–0.98) |
| PG-TXL 80 mg eq./kg | Yes | 62 ± 4.6 | 45.6 | 37.5 ± 4.6 | 1.8 (1.5–2.2) |
| PG-TXL 120 mg eq/kg | Yes | 115 ± 3 | 98.4 | 85.9 ± 3.0 | 4.2 (3.9–4.3)[e] |
| PG-TXL 120 mg eq/kg | Yes[d] | 117 ± 1.2 | 100.5 | 88 ± 1.2 | 4.3 (4.1–4.4)[e] |

[a]Absolute growth delay is defined as the time in days for tumors in treated groups to grow from 8 to 14 mm minus the time in days for tumors in saline treated group to grow from 8 to 14 mm.
[b]Normalized growth delay is defined as the time in days for tumors to grow from 8 to 14 mm in mice treated with the combination of PG-TXL and radiation minus the time in days for tumors to grow from 8 to 14 mm in mice treated with PG-TXL alone.
[c]Enhancement factors are obtained by dividing normalized tumor growth delay in mice treated with PG-TXL plus radiation by the absolute growth delay in mice treated with radiation alone.
[d]Radiation was given at 24 h prior to PG-TXL treatment. All other combination groups: radiation was given at 24 h after PG-TXL treatment.
[e]Data based on tumors that had regrown on day 120. Tumors in 2 out of 6 mice for both groups were still not measurable on day 120.

Conclusion

The results of this study indicate that PG-TXL in combination with radiotherapy may be effectively used either before or after irradiation to enhance radiosensitization. These results further suggest that conjugation of radiosensitizers and anti-tumor drugs to water-soluble polymeric carriers may offer enhanced radiosensitization effect. In light of the present disclosures, one of ordinary skill in the art will recognize that doses of PG-TXL and the other compositions disclosed herein, as well as the doses of radiation, either administered externally or internally (i.e. that is to say, radiation administered by an external radiation source, or administered systemically, for example, by injection or ingestion of radioactive materials, such as a radioisotope containing formulation), may be varied. Treatment schedules and dosages may be varied on a patient by patient—basis, taking into account, for example, factors such as the weight and age of the patient, the type of tumor being treated, the severity of the disease condition, previous and/or concurrent therapeutic interventions, the manner of administration and the like, which can be readily determined by one of ordinary skill in the art. For example, it is contemplated that a preferred range of doses for PG-TXL would be from about 0.5× to about 2× the maximum tolerated dose of TXL in equivalent paclitaxel doses. The amount of PG-TXL administered may be spread over the course of radiation therapy as sub-doses. It is also contemplated that a preferred range of irradiation would be about 50 to about 70 Gray (Gy) administered over about 5 to about 7 weeks or about 10 Gray per week. Preferred schedules of administration would include administering PG-TXL about 1 to about 2 days before, or about 1 to about 2 days after irradiation. Schedules of administration of PG-TXL and other polymer-antitumor drug or chelator-antitumor drug compositions, of course, may be varied and/or repeated as determined by one of ordinary skill in the art for the maximum benefit of each patient.

While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are both chemically and physiologically related, as other water soluble polymer-drug conjugates may be substituted for the agents described herein, the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bartoni and Boitard, "In vitro and in vivo antitumoral activity of free, and encapsulated taxol," *J. Microencapsulation*, 7:191–197, 1990.

Berstein, et al., "Higher antitumor efficacy of daunomycin when linked to dextran: In vitro and in vivo studies," *J. Natl. Cancer Inst.*, 60:379–384, 1978, Boyle, et al, "Prevention of taxol induced neuropathy by glutamate," *Cancer Res.*, 37:290. 1996.

Cabral and Barlow, "Resistance to antimitotic agents as genetic probes of microtubule structure and function," *Pharmac. Ther.*, 52:159–171, 1991.

Cabral, Wible, Brenner, Brinkley, "Taxol-requiring mutant of Chinese hamster ovary cells with impaired mitotic spindle assembly," *J. Cell Biol.*, 97:30–39, 1983.

Cortes, J. E. and Pazdur, R., "Docetaxel," *Journal of Clinical Oncology* 13:2643–2655, 1995.

Deutsch et al., "Synthesis of congeners and prodrugs. 3. Water-soluble prodrugs of paclitaxel with potent antitumor activity," *J. Med. Chem.*, 32:788–792, 1989.

Duncan, et al., "Anticancer agents coupled to N-(2hydroxypropyl)methacryamide copolymers. 3. Evaluation of adriamycin conjugates against mouse leukemia L1210 in vivo," *J. Controlled Rel.*, 10:51–63, 1989.

Eiseman et al., "Plasma pharmacokinetics and tissue distribution of paclitaxel in CD2F1 mice," *Cancer Chemother. Pharmacol.*, 34:465–471, 1994.

Fidler, Gersten, Hart, "The biology of cancer invasion and metastasis," *Adv. Cancer Res.*, 28:149–250, 1987.

Foa, Norton, Seidman, "Taxol (paclitaxel): a novel anti-microtubule agent with remarkable anti-neoplastic activity," *Int. J. Clin. Lab. Res.*, 24:6–14, 1994.

Goldspiel, "Taxol pharmaceutical issues: preparation, administration, stability, and compatibility with other medications," *Ann. Pharmacotherapy*, 28:S23–26, 1994.

Greenwald et al., "Highly water soluble taxol derivative: 2'-polyethylene glycol esters as potential products," *Bioorganic & Medicinal Chemistry Letters*, 4:2465–2470, 1994.

Greenwald et al., "Highly water soluble Taxol derivatives, 7-polyethylene glycol esters as potential products," *J. Org. Chem.*, 60:331–336, 1995.

Greenwald, et al., "Drug delivery systems: Water soluble taxol 2'-poly(ethylene glycol) ester prodrugs-design and in vivo effectiveness," *J. Med. Chem.*, 39:424–431, 1996.

Hirano et al., "Polymeric derivatives of activated cyclophosphamide as drug delivery systems in antitumor therapy," *Macromol. Chem.*, 180:1125–1130, 1979.

Hoes et al., "Optimization of macromolecular prodrugs of the antitumor antibiotic adriamycin," *J. Controlled Release*, 2:205–213, 1985.

Holmes, Kudelka, Kavanagh, Huber, Ajani, Valero, "Current status of clinical trials with paclitaxel and docetaxel," In: *Taxane Anticancer Agents: Basic Science and Current Status*, Georg, Chen, Ojima, Vyas, eds., American Chemical Society, Washington, DC, 31–57, 1995.

Horwitz et al., "Taxol, mechanisms of action and resistance," *J. Natl. Cancer Inst. Monographs No. 15*, pp. 55–61, 1993.

Kato, et al., "Antitumor activity of 1-barabinofuranosylcytosine conjugated with polyglutamic acid and its derivative," *Cancer Res.*, 44:25–30, 1984.

Kopecek and Kopeckova. "Targetable water-soluble polymeric anticancer drugs: achievements and unsolved problems," *Proceed. Intern Symp. Control. Rel. Bioact. Mater.*, 20:190–191, 1993.

Kopecek, "The potential of water-soluble polymeric carriers in targeted and site-specific drug delivery," *J. Controlled Release*, 11:279–290, 1990.

Li, et al., "Synthesis and evaluation of water-soluble polyethylene glycol paclitaxel conjugate as a paclitaxel prodrug," *Anti-Cancer Drugs*, 7:642–648, 1996.

Li, Yu, Newman, Cabral, Stephens, Hunter, Milas, Wallace, "Complete regression of well-established tumors using a novel water-soluble poly(L-glutamic acid)paclitaxel conjugate," *Cancer Res.*, 58:2404–2409, 1998.

Liu, et al., "Evidence for involvement of tyrosine phosphorylation in taxol-induced apoptosis in a human ovarian tumor cell line," *Biochem. Pharmacol.*, 48:1265–1272, 1994.

Longnecker, et al., "High performance liquid chromatographic assay for Taxol in human plasma and urine and pharmacokinetics in a phase I trial," *Cancer Treat. Rep.,* 71:53–59, 1987.

Maeda and Matsumura, "Tumoritropic and lymphotropic principles of macromolecular drugs," *Critical Review in Therapeutic Drug Carrier Systems,* 6:193–210, 1989.

Maeda, "SMANCS and polymer-conjugated macromolecular drugs: advantages in cancer chemotherapy," *Adv. Drug Delivery Rev.,* 6:181–193, 1991.

Maeda, Seymour, Miyamoto, "Conjugates of anticancer agents and polymers: Advantages of macromolecular therapeutics in vivo," *Bioconjug. Chem.,* 3:351–362, 1992.

Magri and Kingston, "Modified taxols. 2. Oxidation products of taxol," *J. Org. Chem.,* 51:797–802, 1986.

Mathew et al., "Synthesis and evaluation of some water-soluble prodrugs and derivatives of taxol with antitumor activity," *J. Med. Chem.,* 35:145–151, 1992.

Milas, et al., "Kinetics of mitotic arrest and apoptosis in murine mammary and ovarian tumors treated with taxol," *Proc. Am. Assoc. Cancer Chemother. Pharmacol.,* 35:297–303, 1995.

Mosmann, T., "Rapid colormetric assay for cellular growth and survival: application to proliferation and cytotoxic assay," *J. Immunol. Methods,* 65:55–63, 1983.

Nicolaou, Riemer, Kerr, Rideout, Wrasidio, "Design, synthesis and biological activity of protaxols," *Nature,* 364:464–466, 1993.

Oliver, S. J. et al., Suppression of collagen-induced arthritis using an angiogenesis inhibitor, AGM-1470, and a microtubule stabilizer, Taxol," *Cellular Immunology* 157:291–299, 1994.

Phillips-Hughes and Kandarpa, "Restenosis: pathophysiology and preventive strategies," *JVIR* 7:321–333, 1996.

Reynolds, T., "Polymers help guide cancer drugs to tumor targets- and keep them there," *J. Natl. Cancer Institute,* 87:1582–1584, 1995.

Rose, et al., "Preclinical antitumor activity of water-soluble paclitaxel derivatives," *Cancer Chemother. Pharmacol.,* 39:486–492, 1997.

Rotman, "Chemoirradiation: a new initiative in cancer treatment. 1991 RSNA annual oration in radiation oncology," *Radiology,* 184:319–329, 1992.

Rowinsky and Donehower, "Review: Paclitaxel (Taxol)," *N. Engl. J. Med.,* 332:1004–1014, 1995.

Rowinsky, Chaudhry, Cornblath, Donehower, "Phase I and pharmacologic study of paclitaxel and cisplatin with granulocyte colony-stimulating factor: neuromuscular toxicity is dose-limiting," *J. Clin. Oncol.,* 11:2010–2020, 1993.

Scudiero et al. "Evaluation of a Soluble Tetrazolium/ Formazan Assay for Cell Growth and Drug Sensitivity in Culture Using Human and Other Tumor Cell Lines," *Cancer Research,* 48:4827–4833, 1988.

Serruys, De Jaegere, Kiemeneij et al., "A comparison of balloon-expandable-stent implantation with balloon angioplasty in patients with coronary artery disease," *N. Engl. J. Med.,* 331:489–495, 1994.

Sharma and Straubinger, "Novel taxol formulations: Preparation and Characterization of taxol-containing liposomes," *Pharm. Res.* 11:889–896, 1994.

Trouet, et al., "A covalent linkage between daunorubicin and proteins that is stable in serum and reversible by lysosomal hydrolases, as required for a lysosomotropic drug-carrier conjugate: In vitro and in vivo studies," *Proc. Natl. Acad. Sci. U.S.A.,* 79:626–629, 1982.

U.S. Pat. No. 5,583,153
U.S. Pat. No. 5,362,831
van Heeswijk et al., "The synthesis and characterization of polypeptide-adriamycin conjugate and its complexes with adriamycin. Part 1," *J. Controlled Release,* 1:301–315, 1985.

Vyas et al., "Phosphatase-activated prodrugs of paclitaxel," In:Taxane Anticancer Agents: Basic Science and Current Status, Georg, Chen, Ojima, Vyas. eds., *American Chemical Society,* Washington, DC, 124–137, 1995.

Weiss et al., "Hypersensitivity reactions from Taxol," *J. Clin. Oncol.,* 8:1263–1268, 1990.

Zhao, Z. and Kingston, D. G. I., "Modified taxols. 6. Preparation of water-soluble taxol phosphates," *J. Nat. Prod.,* 54:1607–1611, 1991.

What is claimed is:

1. A method for treating cancer in a subject, comprising administering to a subject having cancer (i) a composition of a taxoid molecule conjugated to a water soluble polymer and (ii) radiation.

2. The method of claim 1, wherein said taxoid is paclitaxel and said water soluble polymer is polyglutamic acid.

3. The method of claim 1, wherein said taxoid is docetaxel and said water soluble polymer is polyglutamic acid.

4. The method of claim 2, wherein said polyglutamic acid has a molecular weight of about 5000 to about 100,000 daltons.

5. The method of claim 4, wherein said polyglutamic acid has a molecular weight of about 20,000 to about 80,000 daltons.

6. The method of claim 5, wherein said polyglutamic acid has a molecular weight of about 25,000 to about 50,000 daltons.

7. The method of claim 6, wherein said polyglutamic acid has a molecular weight of about 35,000 daltons.

8. The method of claim 6, wherein said composition comprises about 37% by weight paclitaxel.

9. The method of claim 6, wherein said composition comprises from about 2% to about 35% by weight of paclitaxel.

10. The method of claim 6, wherein said radiation is gamma radiation.

11. The method of claim 8, wherein said composition is administered prior to said radiation.

12. The method of claim 8, wherein said composition is administered following said radiation.

13. The method of claim 8, wherein 14 GY radiation is administered.

14. The method of claim 8, wherein 7 GY radiation is administered.

15. The method of claim 8, wherein 10 GY radiation is administered.

16. The method of claim 15, wherein said 10 GY radiation is administered weekly.

17. The method of claim 16, wherein 50 to 70 Gray is administered over 5 to 7 weeks.

18. The method of claim 6, wherein said cancer is breast cancer, ovarian cancer, malignant melanoma, lung cancer, gastric cancer, prostate cancer, colon cancer, head and neck cancer, leukemia or Kaposi's sarcoma.

19. The method of claim 11, wherein said cancer is breast cancer, ovarian cancer, malignant melanoma, lung cancer, gastric cancer, prostate cancer, colon cancer, head and neck cancer, leukemia or Kaposi's sarcoma.

20. The method of claim 12, wherein said cancer is breast cancer, ovarian cancer, malignant melanoma, lung cancer, gastric cancer, prostate cancer, colon cancer, head and neck cancer, leukemia or Kaposi's sarcoma.

21. The method of claim 1, wherein said polymer has a molecular weight of about 20000 to 80000 daltons.

22. The method of claim 1, wherein said polymer has a molecular weight of about 25000 to 50000 daltons.

23. A method of enhancing the response of a tumor to irradiation, comprising:
   a) administering to a patient in need of such therapy a radiosensitizing amount of a pharmaceutical composition comprising paclitaxel, docetaxel, etoposide, teniposide, camptothecin or epothilone conjugated to a water soluble polyamino acid polymer and a pharmaceutically acceptable carrier;
   b) irradiating said tumor;
   wherein said polymer has a molecular weight of about 5000 to 100000 daltons conjugated paclitaxel or docetaxel have increased water solubility, efficacy and accumulation within a tumor compared with the corresponding unconjugated drugs.

24. The method of claim 23, wherein said polymer is polyglutamic acid having a molecular weight of about 20000 to about 80000 and said conjugate comprises about 2% to about 35% by weight of paclitaxel.

25. The method of claim 23, wherein said polymer is polyglutamic acid having a molecular weight of about 20000 to about 80000 and said conjugate comprises about 2% to about 35% by weight of docetaxel.

* * * * *

UNITED STATES PATENT AND TRADEMARK OFFICE
CERTIFICATE OF CORRECTION

PATENT NO. : 6,730,699 B2
DATED : May 4, 2004
INVENTOR(S) : Chun Li et al.

It is certified that error appears in the above-identified patent and that said Letters Patent is hereby corrected as shown below:

<u>Title page,</u>
Item [63], Related U.S. Application Data, should read:
-- Continuation of application No. 10/153,818, filed on May 24, 2002, now Pat. No. 6,515,017, which is a continuation of application No. 09/530,601, filed on Jan. 11, 2001, now abandoned, which claims priority from PCT/US99/06870 filed March 30, 1999, which is based on application No. 09/050,662 filed March 30, 1998, now. Pat. No. 6,441,025 --.

Signed and Sealed this

Eighteenth Day of October, 2005

JON W. DUDAS
*Director of the United States Patent and Trademark Office*